(12) United States Patent
Koch et al.

(10) Patent No.: US 6,242,450 B1
(45) Date of Patent: Jun. 5, 2001

(54) 5-HT$_{1F}$ ANTAGONISTS

(75) Inventors: Daniel James Koch, Indianapolis; Lee Alan Phebus, Fountaintown; Vincent Patrick Rocco, Indianapolis; Tammy Joy Sajdyk, Speedway, all of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/335,083

(22) Filed: Jun. 17, 1999

Related U.S. Application Data
(60) Provisional application No. 60/094,309, filed on Jul. 27, 1998.

(51) Int. Cl.[7] .................. A61K 31/495; A61K 31/47; C07D 241/36; C07D 455/06; C07D 211/06
(52) U.S. Cl. .................. 514/255.04; 514/294; 514/307; 514/308; 514/314; 514/315; 514/318; 544/349; 546/95; 546/96; 546/140; 546/144; 546/167; 546/192; 546/195; 546/196; 546/207
(58) Field of Search .................... 514/315, 318, 514/314, 307, 308, 294, 255.04; 544/349; 546/95, 96, 140, 144, 167, 196, 195, 192, 207

(56) References Cited

U.S. PATENT DOCUMENTS
| | | | |
|---|---|---|---|
| 4,304,912 | 12/1981 | Schroter et al. | 544/405 |
| 4,315,939 | 2/1982 | Frickel et al. | 424/267 |
| 5,614,523 | 3/1997 | Audia et al. | 514/252 |

FOREIGN PATENT DOCUMENTS
| | | |
|---|---|---|
| 2630152 | 1/1978 | (DE) . |
| 95/25721 | * 9/1995 | (WO) . |

* cited by examiner

Primary Examiner—D. Margaret Seaman
(74) Attorney, Agent, or Firm—Robert D. Titus

(57) ABSTRACT

This invention provides 5-HT$_{1f}$ antagonists of Formula I:

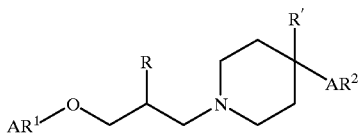

where $AR^1$, $AR^2$, R, and R' are as defined in the specification.

13 Claims, No Drawings

5-HT$_{1F}$ ANTAGONISTS

PRIORITY INFORMATION

This application claims the priority benefit of U.S. Provisional Patent Application Ser. No. 60/094,309 filed Jul. 27, 1998.

BACKGROUND OF THE INVENTION

Serotonin (5-HT) exhibits diverse physiological activity mediated by at least four receptor classes, the most heterogeneous of which appears to be 5-HT$_1$. A human gene which expresses a fifth 5-HT$_1$ subtype, named 5-HT$_{1F}$, was isolated by Kao and coworkers (*Proc. Natl. Acad. Sci. USA*, 90, 408–412 (1993)). This 5-HT$_{1F}$ receptor exhibits a pharmacological profile distinct from any serotonergic receptor yet described. While 5-HT$_{1F}$ agonists have been reported by Audia and Nissen (U.S. Pat. No. 5,521,196) and Audia (U.S. Pat. No. 5,521,197), antagonists of the 5-HT$_{1F}$ receptor, and their pharmacological activity, were heretofore unknown. This invention provides novel 5-HT$_{1F}$ antagonists which are useful for the treatment of anxiety disorders.

SUMMARY OF THE INVENTION

The present invention provides the substituted piperidines of formula I:

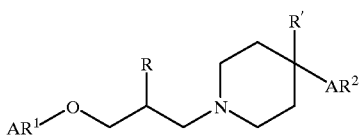

I where:
R and R' are independently hydrogen or hydroxy;
AR$^1$ is phenyl, naphthyl, quinolinyl, isoquinolinyl, indanyl, 1,2,3,4-tetrahydronaphthyl, indolyl, N-(C$_1$–C$_4$ alkyl)indolyl, benzothiazolyl, benzothienyl, benzofuryl, 2,3-dihydrobenzothienyl, 2,3-dihydrobenzofuryl, julolidinyl, or dibenzofuryl, each optionally substituted with one or two substituents independently selected from the group consisting of C$_1$–C$_6$ alkyl, C$_1$–C$_6$ acyl, benzoyl, C$_1$–C$_6$ alkoxy, phenoxy, C$_1$–C$_6$ alkylthio, trifluoromethyl, trifluoromethoxy, or halo;
AR$^2$ is pyridin-3-yl, quinolin-3-yl, isoquinolin-4-yl, or quinoxalin-2-yl; and pharmaceutically acceptable acid addition salts thereof.

A further embodiment of this invention is a method for decreasing activation of the 5-HT$_{1F}$ receptor by administering a compound of Formula I.

Antagonism of the 5-HT$_{1F}$ receptor provides a method for treating anxiety disorders. A further embodiment of this invention is a method for the treatment of anxiety disorders, comprising administering to a mammal in need of such treatment an effective dose of a compound of Formula I.

In addition, this invention provides pharmaceutical formulations comprising an effective amount for deactivation of the 5-HT$_{1F}$ receptor of a compound of Formula I, in combination with a suitable pharmaceutical carrier, diluent, or excipient.

This invention also provides the use of a compound of Formula I for the manufacture of a medicament for the treatment of anxiety disorders. Additionally, this invention provides a pharmaceutical formulation adapted for the treatment of anxiety disorders containing a compound of Formula I.

DETAILED DESCRIPTION

The general chemical terms used in the formulae above have their usual meanings. For example, the term "alkyl" includes such groups as methyl, ethyl, n-propyl, isopropyl, n-butyl, isobutyl, sec-butyl, tert-butyl, 1-pentyl, 2-pent-yl, 3-pentyl, neopentyl, hexyl, and the like. The term "alkoxy" includes methoxy, ethoxy, isopropoxy, butoxy, tert-butoxy, hexyloxy, and the like. The term "alkylthio" includes methylthio, ethylthio, isopropylthio, butylthio, tert-butylthio, hexylthio, and the like. The term "acyl" includes formyl, acetyl, propanoyl, butanoyl, 2-methylpropanoyl, pentanoyl, and the like. The term "halo" includes fluoro, chloro, bromo and iodo.

The compounds of the invention where R is hydroxy possess an asymmetric carbon labelled with an asterisk in the following formula:

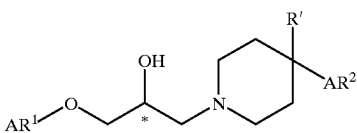

As such, each of the compounds of the present invention exists not only as the racemate but as individual R- and S-enantiomers as well:

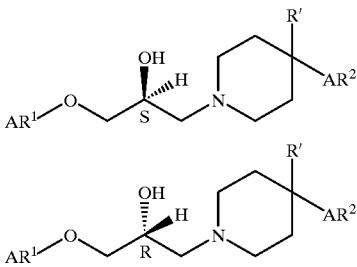

The compounds of the present invention include the individual R- and S-enantiomers, and mixtures thereof, including the racemates.

The compounds of this invention are useful in a method for decreasing activation of the 5-HT$_{1F}$ receptor for treating disorders which have been linked to excessive neurotransmission of serotonin in mammals. It is preferred that the mammal to be treated by the administration of compounds of this invention is human.

While all of the compounds of the present invention are useful as 5-HT$_{1F}$ antagonists, certain classes are preferred. The following paragraphs describe such preferred classes.

aa) R is hydroxy;
ab) R' is hydroxy;
ac) R and R' are both hydroxy;
ad) AR$^1$ is phenyl;
ae) AR$^1$ is indolyl;
af) AR$^1$ is indol-4-yl;
ag) AR$^1$ is indol-5-yl;
ah) AR$^1$ is N-(C$_1$–C$_4$ alkyl)indolyl;
ai) AR$^1$ is substituted phenyl;
aj) AR$^1$ is monosubstituted phenyl;
ak) AR$^1$ is phenyl monosubstituted with trifluoromethyl, C$_1$–C$_6$ alkyl, C$_1$–C$_6$ alkoxy, C$_1$–C$_6$ alkylthio, or halo;
al) AR$^1$ is phenyl monosubstituted with trifluoromethyl;

am) AR$^1$ is phenyl monosubstituted with C$_1$–C$_6$ alkoxy;
an) AR$^1$ is phenyl monosubstituted with methoxy;
ao) AR$^1$ is 4-methoxyphenyl;
ap) AR$^1$ is 4-benzyloxyphenyl;
aq) AR$^1$ is phenyl monosubstituted with C$_1$–C$_6$ alkyl;
ar) AR$^1$ is phenyl monosubstituted with methyl, ethyl, isopropyl, or tert-butyl;
as) AR$^1$ is phenyl monosubstituted in the 4-position with methyl, ethyl, isopropyl, or tert-butyl;
at) AR$^1$ is 2-tert-butylphenyl;
au) AR$^1$ is phenyl monosubstituted with halo;
av) AR$^1$ is phenyl monosubstituted in the 4-position with halo;
aw) AR$^1$ is 4-chlorophenyl;
ax) AR$^1$ is 4-iodophenyl;
ay) AR$^1$ is disubstituted phenyl;
az) AR$^1$ is 2,4-disubstituted phenyl;
ba) AR$^1$ is phenyl disubstituted with C$_1$–C$_6$ alkyl;
bb) AR$^1$ is phenyl disubstituted with methyl;
bc) AR$^1$ is 2,4-dimethylphenyl;
bd) AR$^1$ is 2-methoxy-4-methylphenyl;
be) AR$^1$ is 2-methyl-4-methylthiophenyl;
bf) AR$^1$ is 2-methyl-4-acetylphenyl;
bg) AR$^1$ is naphthyl;
bh) AR$^1$ is naphth-2-yl;
bi) AR$^1$ is 6-methoxynaphth-2-yl;
bj) AR$^1$ is indanyl;
bk) AR$^1$ is substituted indanyl;
bl) AR$^1$ is 7-methylindan-4-yl;
bm) AR$^1$ is 1,2,3,4-tetrahydronaphth-6-yl;
bn) AR$^1$ is quinolinyl;
bo) AR$^1$ is quinolin-6-yl;
bp) AR$^1$ is quinolin-7-yl;
bq) AR$^1$ is dibenzofur-3-yl;
br) AR$^2$ is quinolin-3-yl;
bs) AR$^2$ is quinoxalin-2-yl;
bt) AR$^2$ is pyridin-3-yl;
bu) The compound is a racemate;
bv) The compound is the R-enantiomer;
bw) The compound is the S-enantiomer;
bx) The compound is the free base;
by) The compound is a salt;
bz) The compound is the oxalate salt.

It will be understand that the above preferred classes may be combined to form additional preferred classes.

Since the compounds of this invention are amines, they are basic in nature and accordingly react with any of a number of inorganic and organic acids to form pharmaceutically acceptable acid addition salts. Since many of the free amines of the compounds of this invention are oils or low melting amorphous solids, it is preferable to convert the free amines to their pharmaceutically acceptable acid addition salts for ease of handling and administration. Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methane-sulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulf-ate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with oxalic acid.

The following group is illustrative of compounds contemplated within the scope of this invention:

1-(3-phenoxyprop-1-yl)-4-hydroxy-4-(isoquinolin-4-yl) piperidine oxalate;
1-(3-(2-isopropylphenoxy)prop-1-yl)-4-hydroxy-4-(pyridin-3-yl)piperidine hydrochloride;
1-(3-(3,4-diethylphenoxy)prop-1-yl)-4-hydroxy-4-(quinoxalin-3-yl)piperidine;
1-(3-(2,4-diisopropoxyphenoxy)prop-1-yl)-4-(quinolin-3-yl)piperidine hydrobromide;
1-(3-(2,4-difluorophenoxy)prop-1-yl)-4-(pyridin-3-yl) piperidine;
1-(3-(2-iodo-6-thiomethoxyphenoxy)prop-1-yl)-4-(isoquinolin-4-yl)piperidine trifluoroacetate;
1-(3-(2-butylindol-4-yloxy)prop-1-yl)-4-(quinolin-3-yl) piperidine;
1-(3-(7-trifluoromethylbenzofur-4-yloxy)prop-1-yl)-4-(isoquinolin-4-yl)piperidine methanesulfonate;
1-(3-(3-acetylbenzothien-5-yloxy)prop-1-yl)-4-(pyridin-3-yl)piperidine;
1-(3-(2,2-dimethyl-2,3-dihydrobenzofur-7-yloxy)prop-1-yl)-4-(quinoxalin-4-yl)piperidine benzoate;
1-(3-(julolidin-4-yloxy)prop-1-yl)-4-(isoquinolin-4-yl) piperidine oxalate;
1(3-(6-methoxynaphth-2-yloxy)prop-1-yl)-4-(pyridin-3-yl)piperidine tartarate;
1-((2R,S)-hydroxy-3-phenoxyprop-1-yl)-4-(quinolin-3-yl)piperidine maleate;
1-((2S)-hydroxy-3-(4-methylphenoxy)prop-1-yl)-4-(isoquinolin-4-yl)piperidine;
1-((2R)-hydroxy-3-(4-ethylphenoxy)prop-1-yl)-4-(pyridin-3-yl)piperidine naphthalenesulfonate;
1-((2S)-hydroxy-3-(4-isopropylphenoxy)prop-1-yl)-4-(quinoxalin-2-yl)piperidine mandelate;
1-((2R,S)-hydroxy-3-(4-tert-butylphenoxy)prop-1-yl)-4-hydroxy-4-(isoquinolin-4-yl)piperidine;
1-((2R)-hydroxy-3-(4-chlorophenoxy)prop-1-yl)-4-hydroxy-4-(pyridin-3-yl)piperidine phenylsulfonate;
1-((2S)-hydroxy-3-(4-iodophenoxy)prop-1-yl)-4-hydroxy-4-(quinoxalin-3-yl)piperidine;
1-((2S)-hydroxy-3-(4-trifluoromethylphenoxy)prop-1-yl)-4-hydroxy-4-(isoquinolin-4-yl)piperidine;
1-((2R,S)-hydroxy-3-(2-methoxyphenoxy)prop-1-yl)-4-hydroxy-4-(pyridin-3-yl)piperidine 4-chlorobenzoate;
1-((2R)-hydroxy-3-(3-methoxyphenoxy)prop-1-yl)-4-hydroxy-4-(quinoxalin-3-yl)piperidine;
1-((2S)-hydroxy-3-(4-methoxyphenoxy)prop-1-yl)-4-hydroxy-4-(isoquinolin-4-yl)piperidine acrylate;
1-((RS)-hydroxy-3-(4-trifluoromethoxyphenoxy)prop-1-yl)-4-hydroxy-4-(pyridin-3-yl)piperidine ;
1-((2R)-hydroxy-3-(4-phenoxyphenoxy)prop-1-yl)-4-hydroxy-4-(quinoxalin-2-yl)piperidine heptanoate;

1-((2R)-hydroxy-3-(2-methylthiophenoxy)prop-1-yl)-4-hydroxy-4-(isoquinolin-4-yl)piperidine succinate;

1-((2R,S)-hydroxy-3-(4-methylthiophenoxy)prop-1-yl)-4-hydroxy-4-(pyridin-3-yl)piperidine sebacate;

1-((2R)-hydroxy-3-(2,3-dimethylphenoxy)prop-1-yl)-4-hydroxy-4-(quinoxalin-2-yl)piperidine fumarate;

1-((2S)-hydroxy-3-(3,4-dimethylphenoxy)prop-1-yl)-4-hydroxy-4-(isoquinolin-4-yl)piperidine malonate;

1-((2S)-hydroxy-3-(2,4-dimethylphenoxy)prop-1-yl)-4-hydroxy-4-(pyridin-4-yl)piperidine butyne-1,4-dioate;

1-((2R)-hydroxy-3-(2,4-dichlorophenoxy)prop-1-yl)-4-hydroxy-4-(quinoxalin-2-yl)piperidine;

1-((2R,S)-hydroxy-3-(2-methoxy-4-methylphenoxy)prop-1-yl)-4-hydroxy-4-(quinoxalin-3-yl)piperidine 2,4-dinitrobenzoate;

1-((2R)-hydroxy-3-(2-methyl-4-methylthiophenoxy)-prop-1-yl)-4-hydroxy-4-(isoquinolin-4-yl)piperidine;

1-((2S)-hydroxy-3-(3-methyl-4-acetylphenoxy)prop-1-yl)-4-hydroxy-4-(pyridin-3-yl)piperidine;

1-((2S)-hydroxy-3-(2-methyl-4-acetylphenoxy prop-1-yl)-4-hydroxy-4-(quinoxalin-2-yl)piperidine 2-hydroxybenzoate;

1-((2S)-hydroxy-3-(2-benzoyl-4-methylphenoxy)prop-1-yl)-4-hydroxy-4-(isoquinolin-4-yl)piperidine;

1-((2R)-hydroxy-3-(naphth-2-yloxy)prop-1-yl)-4-hydroxy-4-(isoquinolin-4-yl)piperidine;

1-((2R,S)-hydroxy-3-(6-methoxynaph-2-yloxy)prop-1-yl)-4-hydroxy-4-(isoquinolin-4-yl)piperidine phthalate;

1-((2R)-hydroxy-3-(6,7-dichloroindol-4-yloxy)prop-1-yl)-4-hydroxy-4-(isoquinolin-4-yl)piperidine phenylacetate;

1-((2S)-hydroxy-3-(2-isopropylindol-5-yloxy)prop-1-yl)-4-hydroxy-4-(pyridinin-3-yl)piperidine citrate;

1-((2R)-hydroxy-3-(2-methyl-7-chloroindol-5-yloxy)prop-1-yl)-4-hydroxy-4-(quinoxalin-3-yl)piperidine lactate;

1-((2R,S)-hydroxy-3-(1-isopropyl-6-methyl-7-chloroindol-4-yloxy)prop-1-yl)-4-hydroxy-4-(isoquinolin-4-yl)piperidine glycollate;

1-((2S)-hydroxy-3-(2-ethylindol-4-yloxy)prop-1-yl)-4-hydroxy-4-(pyridin-3-yl)piperidine;

1-((2R)-hydroxy-3-(2,6-dimethylbenzofur-4-yloxy)-prop-1-yl)-4-hydroxy-4-(quinoxalin-2-yl)piperidine;

1-((2S)-hydroxy-3-(6-trifluoromethylbenzothien-4-yloxy)prop-1-yl)-4-hydroxy-4-(isoquinolin-4-yl)piperidine hydrobromide;

1-((2R,S)-hydroxy-3-(2-methylbenzothiazol-5-yloxy)-prop-1-yl)-4-hydroxy-4-(pyridin-3-yl)piperidine mandelate;

1-((2S)-hydroxy-3-(6,7-difluoroindan-4-yloxy)prop-1-yl)-4-hydroxy-4-(isoquinolin-4-yl)piperidine citrate;

1-((2R,S)-hydroxy-3-(4-methylthioindan-5-yloxy)prop-1-yl)-4-hydroxy-4-(pyridin-3-yl)piperidine;

1-((2R)-hydroxy-3-(7-methylindan-4-yloxy)prop-1-yl)-4-hydroxy-4-(quinoxalin-2-yl)piperidine;

1-((2S)-hydroxy-3-(1,2,3,4-tetrahydronaphth-6-yloxy)prop-1-yl)-4-hydroxy-4-(isoquinolin-4-yl)-piperidine;

1-((2R)-hydroxy-3-(2-methylquinolin-6-yloxy)prop-1-yl)-4-hydroxy-4-(pyridin-3-yl)piperidine;

1-((2S)-hydroxy-3-(quinolin-7-yloxy)prop-1-yl)-4-hydroxy-4-(quinoxalin-2-yl)piperidine;

1-((2S)-hydroxy-3-(julolidin-7-yloxy)prop-1-yl)-4-hydroxy-4-(isoquinolin-4-yl)piperidine;

1-((2S)-hydroxy-3-(5-methyl-6-bromodibenzofur-3-yloxy)prop-1-yl)-4-hydroxy-4-(pyridin-3-yl)piperidine hydroiodide;

1-((2R)-hydroxy-3-(carbazol-2-yloxy)prop-1-yl)-4-hydroxy-4-(quinoxalin-3-yl)piperidine sulfate;

1-((2S)-hydroxy-3-(6-methoxy-7-chloroindol-4-yloxy)prop-1-yl)-4-hydroxy-4-(isoquinolin-4-yl)piperidine;

1-((2R)-hydroxy-3-(1-ethyl-7-trifluoromethylindol-4-yloxy)prop-1-yl)-4-hydroxy-4-(pyridin-3-yl)piperidine;

1-((2R,S)-hydroxy-3-(5,6-dichloroindol-4-yloxy)prop-1-yl)-4-(quinoxalin-3-yl)piperidine.

The compounds of the present invention are prepared by standard synthetic organic chemistry methodology as illustrated in Synthetic Scheme I, where $AR^1$, $AR^2$, and $R^1$ are as previously defined.

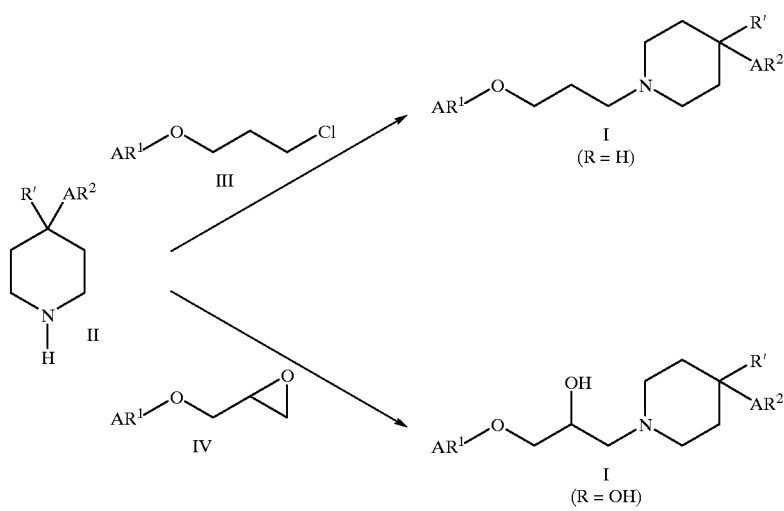

Synthetic Scheme I

Compounds of the invention where R is hydrogen are prepared by reacting a substituted piperidine of Formula II with a 3-chloropropyl $AR^1$ ether of Formula III under standard alkylation conditions. The requisite piperidine and chloropropyl ether are combined in a mutual solvent, typically acetonitrile, with an appropriate base, typically potassium or sodium carbonate. The reaction is performed at a temperature from about room temperature to about reflux until complete. At reflux temperature, the reactions are typically complete in from about 12 to about 48 hours. The compounds of the invention are then isolated by standard extractive workup and purified by chromatography or crystallization as appropriate. Pharmaceutically acceptable salts are then prepared if necessary or desired under standard conditions.

Compounds of the invention where R is hydroxy are prepared by reacting a substituted piperidine of Formula II with a glycidyl $AR^1$ ether of Formula IV under standard nucleophilic displacement conditions. The requisite piperidine and glycidyl ether are combined in a mutual solvent, typically methanol, and the mixture heated to about reflux until the reaction is complete. At reflux temperatures, the reactions are typically complete in from 12 to 48 hours. The compounds of the invention are then isolated by standard extractive workup and purified by chromatography or crystallization as appropriate. Pharmaceutically acceptable salts are then prepared if necessary or desired under standard conditions.

The 3-chloropropyl $AR^1$ ethers of Formula III are prepared by O-alkylation of an appropriate $AR^1$ alcohol with 1-bromo-3-chloropropane as illustrated in Synthetic Scheme II, where $AR^1$ is as previously defined.

Synthetic Scheme II

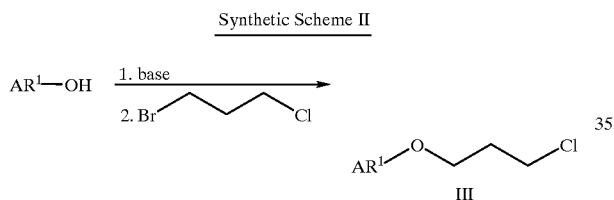

An appropriate alcohol is deprotonated with a suitable base, typically sodium hydride, in a suitable solvent, typically dimethylformamide, at from about 0° C. to about room temperature. The resultant anion is then reacted with 1-bromo-3-chloropropane at about room temperature for from about 1 hour to about 2 days. The desired chloropropyl ether is isolated by normal extractive workup. The compound may be used as isolated for subsequent reactions, or purified by chromatography if necessary or desired.

The 3-glycidyl $AR^1$ ethers of Formula IV are prepared by reaction of an appropriate $AR^1$ alcohol with a glycidyl-3-nitrobenzenesulfonate as illustrated in Synthetic Scheme III, where $AR^1$ is as previously defined.

Synthetic Scheme III

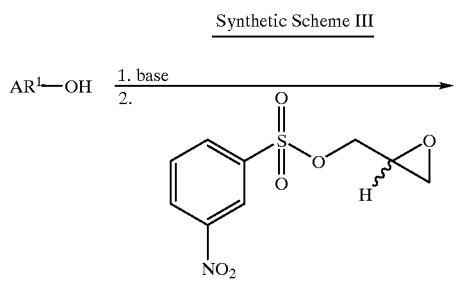

-continued

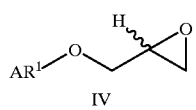

The requisite anion is prepared as described supra and is then reacted with with an appropriate glycidyl-3-nitrobenzenesulfonate at room temperature for from about 1 to about 24 hours. The desired glycidyl ether is isolated by normal extractive workup. The compound may be used as isolated for subsequent reactions, or purified by chromatography or crystallization if necessary or desired.

The compounds of Formula II where R' is hydroxy are prepared by the procedure illustrated in Synthetic Scheme IV, where halide is chloro, bromo or iodo and $AR^2$ is as previously defined.

Synthetic Scheme IV

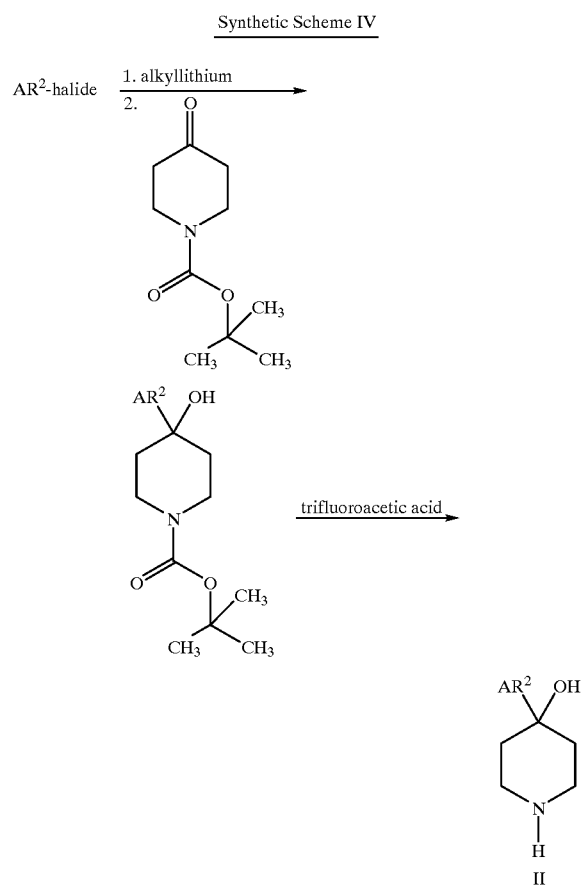

An appropriate $AR^2$-halide is reacted with an alkyllithium, typically n-butyllithium or sec-butyllithium, at about −100 to about −78° C. for from 1 to about 4 hours in a suitable solvent, such as diethyl ether or tetrahydrofuran. To the $AR^2$-Li formed in this manner is added 1-tert-butoxycarbonyl-4-piperdone and the reaction is stirred from about 4 to about 24 hours at room temperature. The resultant alcohol is isolated by extractive workup may be used as isolated for subsequent reactions or purified by chromatography if necessary. The alcohol is N-deprotected by reaction with trifluoroacetic acid in a suitable solvent, typically dichloromethane, at room temperature for from about 4 to about 24 hours. Excess acid is neutralized with an appropriate base, typically sodium or potassium hydroxide, and the desired product isolated by normal extractive work up. The 4-hydroxypiperidine may be used as is or purified by chromatography if necessary or desired.

The compounds of Formula II where R' is hydrogen are prepared as illustrated in Synthetic Scheme V where halide and $AR^2$ are as previously defined.

tetrahydropyridine is then hydrogenated in the presence of a precious metal catalyst, typically palladium on carbon, in a suitable solvent, typically a lower alkanol such as methanol or ethanol. The hydrogenation may be performed at about 1 atmosphere at a temperature of from about ambient to reflux. Additional charges of hydrogen may be required to com- Synthetic Scheme V

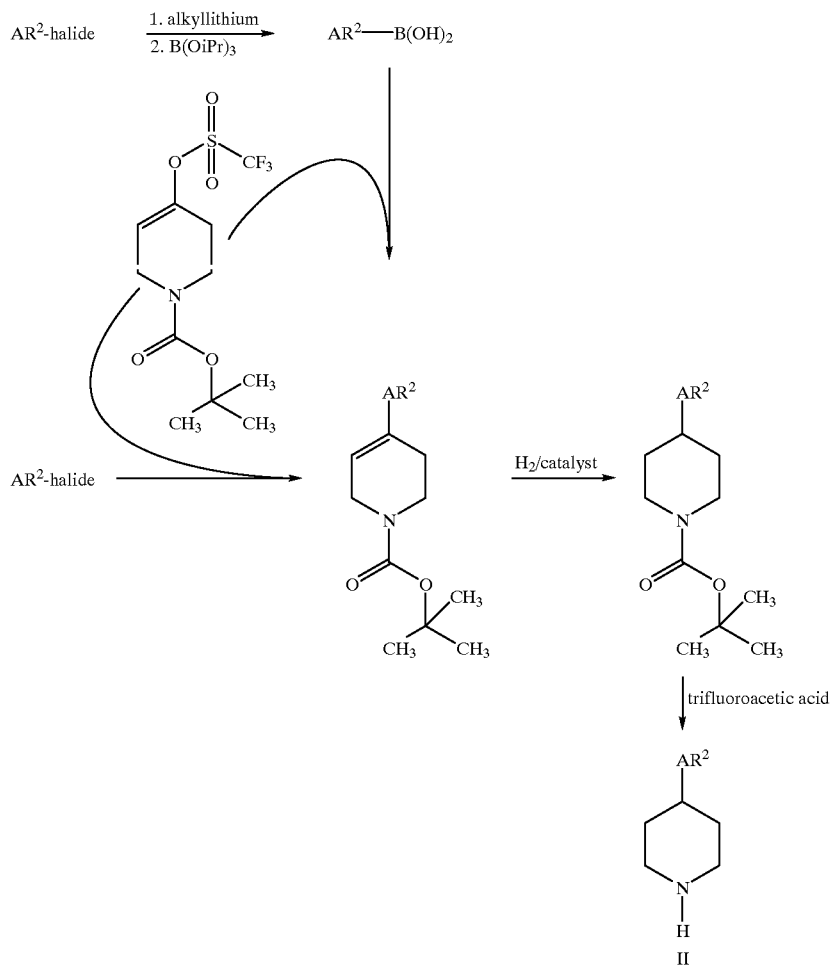

The $AR^2$-halide is reacted with an alkyllithium, typically n-butyllithium or sec-butyllithium, at about −78° C. for from 1 to about 4 hours in a suitable solvent, such as diethyl ether or tetrahydrofuran. To the $AR^2$-Li formed in this manner is added triisopropylborate and the reaction is stirred from about 4 to about 24 hours at room temperature. The resultant alcohol is isolated by extractive workup may be used as isolated for subsequent reactions or purified by chromatography or crystallization if necessary. The resultant boronic acid and 1-tert-butoxycarbonyl-4-trifluoromethanesulfonyloxy-1,2,5,6-tetrahydropyridine are reacted together with [1,1-bis(diphenylphosphino)-1-ferrocene]palladium II chloride in tetrahydrofuran containing lithium chloride, aqueous sodium carbonate and methanol. The reaction is performed at about reflux for from about 1 to about 12 hours. The desired tetrahydropyridine is isolated by standard extractive work up and may be used as isolated for subsequent reactions or purified by chromatography if necessary or desired. The 4-substitutedpletely reduce the double bond. The piperidine product is isolated by filtration of the reaction mixture and concentration under reduced pressure. The N-tert-butyloxycarbonyl protecting group is removed by treatment with trifluoroacetic acid as previously described to provide the 4-substituted piperidines of Formula II.

Where $AR^2$ is quinoxalin-2-yl, the $AR^2$-halide is coupled directly with 1-tert-butoxycarbonyl-4-trifluoromethanesulfonyloxy-1,2,5,6-tetrahydropyridine in the presence of hexamethylditin and [tetrakis(triphenylphosphine)]palladium in 1,4-dioxane containing lithium chloride. The reaction is performed at reflux for about 18 hours. The tetrahydropyridine is isolated and converted to a compound of Formula II by the procedures previously described.

The substituted piperidine intermediates of Formula II:

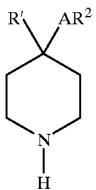

where R' is hydrogen or hydroxy; and AR² is pyridin-3-yl, quinolin-3-yl, isoquinolin-4-yl, or quinoxalin-2-yl represent a further embodiment of the present invention. Compounds of Formula II where R' is hydroxy are preferred. The compound 4-hydroxy-4-(quinolin-3-yl)piperidine is an especially preferred intermediate.

PREPARATION I 1-tert-butoxycarbonyl-4-piperidone

A solution of 9.0 gm (61.5 mMol) 4-piperidone hydrochloride monohydrate in dioxane/water at 0° C. was treated sequentially with aqueous sodium carbonate and 14.4 gm (68 mMol) 2,2-dimethylpropanoic anhydride (BOC anhydride). The resultant slurry was stirred vigorously at room temperature for 18 hours. The reaction mixture was then concentrated under reduced pressure and the residue diluted with ethyl acetate. This mixture was treated with 1.5 M aqueous sodium hydrogen sulfate until the pH was about 2. The layers were separated and the remaining organics were washed with saturated aqueous sodium chloride, dried over sodium sulfate and concentrated under reduced pressure to give 9.8 gm (80%) of the title compound as a tan solid. EA: Calculated for: $C_{10}H_{17}NO_3$: Theory: C, 60.28; H, 8.60;

N, 7.03. Found: C, 60.12; H, 8.54; N, 7.11.

MS(m/e): 199(M⁺).

The glycidyl aryl ethers required for the synthesis of the compounds of the present invention are prepared from the appropriate alcohol by the procedure described in detail in Preparation II.

PREPARATION II (2S)-Glycidyl indol-4-yl ether

A suspension of 0.53 gm (13.3 mMol) sodium hydride (60% dispersion in mineral oil) in 25 mL dimethylformamide was cooled to 0° C. under a nitrogen atmosphere. To this suspension were added 1.62 gm (12.2 mMol) 4-hydroxyindole over 30 minutes and the reaction mixture was allowed to stir at room temperature for 2 hours. To the reaction mixture was then added dropwise a solution of 3.0 gm (11.5 mMol)-(2S)-(+)-glycidyl-3-nitrobenzenesulfonate (Aldrich Chemical Co., Milwaukee, Wis., USA) in 10 mL dimethylformamide and the resulting mixture was stirred at room temperature for an additional 1.5 hours. The reaction mixture was then diluted with 100 mL water and extracted well with ethyl acetate. The ethyl acetate phases were combined, washed sequentially with water and saturated aqueous sodium chloride, dried over sodium sulfate and concentrated under reduced pressure. The residual oil was subjected to flash silica gel chromatography, eluting with dichloromethane. Fractions containing product were combined and concentrated under reduced pressure to provide 1.34 gm (62%) of the title compound as a yellow solid.

PREPARATION III (2S)-Glycidyl 1-methylindol-4-yl ether

A suspension of 0.111 gm (0.28 mMol) sodium hydride (60% dispersion in mineral oil) in dimethylformamide was cooled to 0° C. under a nitrogen atmosphere. To this suspension were added 0.50 gm (2.6 mmol) (2S)-glycidyl indol-4-yl ether and the reaction mixture was stirred for 20 minutes at room temperature. To the reaction mixture were then added 0.17 mL (2.8 mMol) iodomethane and the mixture was stirred at room temperature for 18 hours. The reaction mixture was diluted with water and then extracted well with ethyl acetate. The ethyl acetate phases were combined, washed sequentially with water and saturated aqueous sodium chloride, dried over sodium sulfate and concentrated under reduced pressure. The residue was subjected to flash silica gel chromatography, eluting with 20% ethyl acetate in hexane. Fractions containing product were combined and concentrated under reduced pressure to provide 0.376 gm (70%) of the title compound as a white, waxy solid.

The 3-chloropropyl aryl ethers required for the synthesis of the compounds of the present invention are prepared from the appropriate alcohol by the procedure described in detail in Preparation III.

PREPARATION IV 3-chloropropyl indol-4-yl ether

A suspension of 1.6 gm (39.7 mMol) sodium hydride (60% dispersion in mineral oil) in 80 mL dimethylformamide was cooled to 0° C. under a nitrogen atmosphere. To this suspension were added 5.0 gm (37.6 mMol) 4-hydroxyindole in portions over 30 minutes. The reaction mixture was stirred at room temperature for 1.5 hours after this addition was complete. To the resulting mixture was then added dropwise a solution of 5.91 gm (37.6 mMol) 1-bromo-3-chloropropane in dimethylformamide and the reaction mixture stirred for 18 hours at room temperature. The reaction mixture was diluted with water and then extracted well with ethyl acetate. The ethyl acetate phases were combined, washed sequentially with water and saturated aqueous sodium chloride, dried over sodium sulfate and concentrated under reduced pressure. The residue was subjected to flash silica gel chromatography, eluting with 10% ethyl acetate in hexane. Fractions containing product were combined and concentrated under reduced pressure to provide 4.62 gm (59%) of the title compound.

The 4-aryl-4-hydroxypiperidines required for the synthesis of the compounds of the present invention are prepared from the appropriate aryl halide and N-protected-4-piperidone by the procedure described in detail in Preparation IV.

PREPARATION V 4-(isoquinolin-4-yl)-4-hydroxypiperidine

A solution of 6.46 gm (31.1 mMol) 4-bromoisoquinoline in 80 mL tetrahydrofuran was cooled to −100° C. under a nitrogen atmosphere. To this solution was added dropwise 28.7 mL (37.3 mmol) sec-butyllithium (1.3 M in hexanes) and the reaction mixture was allowed to stir for 1.5 hours. To the reaction mixture was then added dropwise a solution of 1-tert-butoxycarbonyl-4-piperidone in 20 mL tetrahydrofuran dropwise. The reaction mixture was then stirred for 18 hours at room temperature. The reaction mixture was then partitioned between ethyl acetate and 2N sodium hydroxide. The phases were separated and the aqueous phase extracted well with ethyl acetate. The organic phases were combined, washed saturated aqueous sodium chloride, dried over sodium sulfate and concentrated under reduced pressure. The residue was subjected to silica gel chromatography, eluting with 9:1 dichloromethane:methanol. Fractions containing product were combined and concentrated under reduced pressure to provide 3.95 gm (39%) 1-tert-butoxycarbonyl-4-(isoquin-olin-4-yl)-4-hydroxypiperidine as a yellow solid.

A mixture of 2.0 gm (6.1 mMol) 1-tert-butoxycarbon-yl-4-(isoquinolin-4-yl)-4-hydroxypiperidine, and 4 mL trifluoroacetic acid in 20 mL dichloromethane was stirred at room temperature for 18 hours. The reaction mixture was diluted with 2N sodium hydroxide and the phases were separated. The aqueous phase was extracted well with dichloromethane. The organic phases were combined, washed with saturated aqueous sodium chloride, dried over sodium sulfate and concentrated under reduced pressure. The residue was subjected to flash silica gel chromatography, eluting with dichloromethane containing from 10% to 40% methanol and a trace of ammonium hydroxide Fractions containing product were combined and concentrated under reduced pressure to provide 0.793 gm (57%) of the title compound as a light yellow solid.

MS(m/e): 228($M^+$); Calculated for $C_{14}H_{16}N_2O$-0.25 $H_2O$: Theory: C, 72.94; H, 7.10; N, 12.15. Found: C, 72.97; H, 7.09; N, 12.26.

PREPARATION VI 4-(quinolin-3-yl)-4-hydroxypiperidine

Beginning with 7.46 gm (35.9 mMol) 3-bromoquinoline, 7.25 gm (62%) N-tert-butoxycarbonyl-4-(quinolin-3-yl)-4-hydroxypiperidine were recovered as a light yellow solid by the procedure described in detail in Preparation IV.

Beginning with 1.5 gm (4.6 mMol) N-tert-butoxy-carbonyl-4-(quinolin-3-yl)-4-hydroxypiperidine, 0.645 gm (62%) of the title compound were recovered as a light tan solid by the procedure described in detail in Preparation IV.

MS(m/e): 228($M^+$); Calculated for $C_{14}H_{16}N_2O$-0.25 $H_2O$: Theory: C, 72.23; H, 7.14; N, 12.03. Found: C, 72.41; H, 7.12; N, 12.89.

PREPARATION VII 1-tert-butoxycarbonyl-4-trifluoromethanesulfonyloxy-1,2,5,6-tetrahydropyridine A solution of 1.2 mL (8.2 mMol) diisopropylamine in 15 mL tetrahydrofuran was cooled to −78° C. To this solution were added dropwise 5 mL (7.9 mMol) n-butyllithium (1.6 M in hexanes) and the reaction mixture was stirred for 1.5 hours at −78° C. and was then allowed to warm to room temperature. The resulting solution was cooled again to −78° C. and then a solution of 1.56 gm (7.8 mMol) N-tert-butoxycarbonyl-4-piperidone in tetrahydrofuran was added dropwise. After about 30 minutes, a solution of 3.0 gm (8.4 mMol) N-phenyltrifluoromethane-sulfonimide in tetrahydrofuran was added dropwise. The reaction mixture was allowed to warm gradually to room temperature and was then concentrated under reduced pressure. The residue was dissolved in dichloromethane and placed on a pad of neutral alumina. The alumina column was eluted with 9:1 hexane-:ethyl acetate. Fractions containing product were combined and concentrated under reduced pressure to provide 2.24 gm (86%) of the title compound as an oil.

PREPARATION VIII 4-(isoquinolin-4-yl)piperidine oxalate

A solution of 2.0 gm (9.6 mMol) 4-bromoisoquinoline in 30 mL tetrahydrofuran was cooled to −100° C. To this solution were added dropwise 6.3 mL (10.1 mMol) n-butyl-lithium (1.6 M in hexane) dropwise, and the resultant solution was stirred for 30 minutes. To this solution was then added dropwise a solution of 4.4 mL (19.2 mMol) triiso-propylborate and the reaction mixture was then stirred for 18 hours at room temperature. The reaction mixture was then partitioned between ethyl acetate and saturated aqueous sodium chloride. The phases were separated and the aqueous phase extracted well with ethyl acetate. The combined organic phases were washed with saturated aqueous sodium chloride, dried over sodium sulfate and concentrated under reduced pressure. The residue was sonicated in a mixture of hexane:ethyl acetate. The resulting suspension was filtered to provide 0.57 gm (34%) isoquinolin-4-ylboronic acid as a light orange solid.

A mixture of 2.5 gm (14.5 mMol) isoquinolin-4-ylboronic acid, 3.43 gm (10.3 mMol) 1-tert-butoxy-carbonyl-4-trifluoromethanesulfonyloxy-1,2,5,6-tetrahydropyridine, 1.3 gm (30.9 mMol) lithium chloride, 0.04 gm (0.05 mMol) [1,1'-bis (diphenylphosphino)-1-ferrocene]-palladium II chloride, and 2 mL 2M aqueous sodium carbonate in about 20 mL tetrahydrofuran containing a few drops of methanol was stirred at reflux for about 4 hours. The reaction was cooled to room temperature and then partitioned between ethyl acetate and 2N sodium hydroxide. The phases were separated and the aqueous phase was extracted well with ethyl acetate. The organic phases were combined, washed with saturated aqueous sodium chloride, dried over sodium sulfate and concentrated under reduced pressure. The residue was subjected to flash silica gel chromatography, eluting with 3:2 hexane:ethyl acetate. Fractions containing product were combined and concentrated under reduced pressure to provide 0.216 gm (57%) 1-tert-butoxycarbonyl-4-(isoquinolin-4-yl)-1,2,5,6-tetrahydropyridine as a light yellow oil.

A mixture of 0.91 gm (2.9 mMol) 1-tert-butoxy-carbonyl-4-(isoquinolin-4-yl)-1,2,5,6-tetrahydropyridine and 0.1 gm 5% palladium on carbon in 40 mL methanol was stirred at room temperature for 3 days under a hydrogen atmosphere. The reaction mixture was then filtered and the filtrate concentrated under reduced pressure. The residue was subjected to flash silica gel chromatography, eluting with 1:1 ethyl acetate:hexane. Fractions containing product were combined and concentrated under reduced pressure to provide 0.57 gm (63%) of 1-tert-butoxycarbonyl-4-(isoquinolin-4-yl)-piperidine as a clear oil.

A mixture of 0.57 gm (1.8 mMol) 1-tert-butoxycarbonyl-4-(isoquinolin-4-yl)piperidine and 6 mL trifluoroacetic acid in 6 mL dichloromethane was stirred at room temperature for 18 hours. The reaction mixture was diluted with 2N sodium hydroxide and the phases were separated. The aqueous phase was extracted well with dichloromethane. The organic phases were combined, washed with saturated aqueous sodium chloride, dried over sodium sulfate and concentrated under reduced pressure. The residue was subjected to flash silica gel chromatography, eluting with dichloromethane containing from 10% to 40% methanol and a trace of ammonium hydroxide. Fractions containing product were combined and concentrated under reduced pressure to provide 0.242 gm (63%) of 4-(isoquinolin-4-yl)piperidine as a tan solid. A portion of this material was converted to the oxalate salt to provide the title compound.

MS(m/e): 212(M$^+$); Calculated for $C_{16}H_{18}N_2O_4$-0.25 $H_2O$: Theory: C, 62.63; H, 6.08; N, 9.13. Found: C, 62.22; H, 5.99; N, 9.04.

PREPARATION IX 4-(quinolin-3-yl)piperidine

Beginning with 3-bromoquinoline, the title compound was recovered as a clear oil by the procedure described in detail in Preparation VII.

MS(m/e): 212(M$^+$).

PREPARATION X 4-(pyridin-3-yl)piperidine

Beginning with 3-bromopyridine, the title compound was recovered as a light tan waxy solid by the procedure described in detail in Preparation VII. A small amount of this material was converted to the oxalate salt.

MS(m/e): 162(M$^+$); Calculated for $C_{12}H_{16}N_2O_4$-0.75 $H_2O$: Theory: C, 54.23; H, 6.07; N, 10.53. Found: C, 54.30; H, 5.96; N, 10.14.

PREPARATION XI 4-(quinoxalin-2-yl)piperidine

A mixture of 1.4 gm (8.5 mMol) 2-chloroquinoxaline, 2.82 gm (8.5 mMol) 1-tert-butoxycarbonyl-4-trifluoromethanesulfonyloxy-1,2,5,6-tetrahydropyridine, 2.8 gm (8.5 mMol) hexamethylditin, 1.08 gm (25.5 mMol) lithium chloride, and 0.491 gm (0.43 mMol) [tetrakis (triphenylphosphine)]palladium in dioxane was stirred at reflux for 18 hours. The reaction mixture was cooled to room temperature and then poured into a mixture of saturated aqueous potassium fluoride and ethyl acetate. After stirring for two hours, the phases were separated. The organic phase was washed with saturated aqueous sodium chloride, dried over magnesium sulfate and concentrated under reduced pressure. The residue was subjected to flash silica gel chromatography, eluting with a gradient of 100:0 to 25:3 hexane:ethyl acetate. Fractions containing product were combined and concentrated under reduced pressure to provide 1.43 gm (54%) 1-tert-butoxy-carbonyl-4-(quinoxalin-2-yl)-1,2,5,6-tetrahydropyridine as a light yellow oil.

A mixture of 0.55 gm (1.8 mMol) 1-tert-butoxycarbonyl-4-(quinoxalin-2-yl)-1,2,5,6-tetrahydropyridine and 0.1 gm 5% palladium on carbon in 10 mL methanol was stirred at room temperature for 45 minutes under a hydrogen atmosphere. The reaction mixture was then filtered and the filtrate concentrated under reduced pressure to provide 0.47 gm (84%) of 1-tert-butoxycarbonyl-4-(quinoxalin-2-yl) piperidine as a yellow oil.

A mixture of 0.47 gm (1.5 mMol) 1-tert-butoxycarbonyl-4-(quinoxalin-2-yl)piperidine and 5 mL trifluoroacetic acid in 5 mL dichloromethane was stirred at room temperature for 18 hours. The reaction mixture was diluted with 2N sodium hydroxide and the phases were separated. The aqueous phase was extracted well with dichloromethane. The organic phases were combined, washed with saturated aqueous sodium chloride, dried over sodium sulfate and concentrated under reduced pressure. The residue was subjected to flash silica gel chromatography, eluting with dichloromethane containing from 10% to 40% methanol and a trace of ammonium hydroxide. Fractions containing product were combined and concentrated under reduced pressure to provide 0.133 gm (42%) of the title compound as a tan foam.

EXAMPLE 1

1-(3-phenoxyprop-1-yl)-4-hydroxy-4-(quinolin-3-yl) piperidine oxalate

A mixture of 0.112 gm (0.7 mMol) 3-chloropropyl phenyl ether, 0.150 gm (0.7 mMol) 4-hydroxy-4-(quinolin-3-yl) piperidine, and 0.136 gm (1.5 mMol) potassium carbonate in 5 mL acetonitrile was heated to reflux for 18 hours. The reaction mixture was then cooled to room temperature and partitioned between ethyl acetate and 2N sodium hydroxide. The phases were separated and the aqueous phase extracted well with ethyl acetate. The combined organic extracts were washed with saturated aqueous sodium chloride, dried over sodium sulfate and concentrated under reduced pressure. The residue was subjected to flash silica gel chromatography, eluting with 25:2 dichloromethane:methanol. Fractions containing product were combined and concentrated under reduced pressure to provide 0.142 gm (60%) of 1-(3-phenoxyprop-1-yl)-4-hydroxy-4-(quinolin-3-yl) piperidine as a light yellow, viscous oil. The oil was converted to the oxalate salt to provide the title compound.

m.p.=76° C.; MS(m/e): 362(M$^+$).

The compounds of Examples 2-12 were prepared by the procedure described in detail in Example 1.

EXAMPLE 2

1-(3-(2-tert-butylphenoxy)prop-1-yl)-4-hydroxy-4-(quinolin-3-yl)piperidine

Beginning with 0.298 gm (1.3 mMol) 3-chloropropyl 2-tert-butylphenyl ether and 0.300 gm (1.3 mMol) 4-hydroxy-4-(quinolin-3-yl)piperidine, 0.212 gm (39%) of the title compound were recovered as a white, waxy solid.

MS(m/e): 418(M$^+$); Calculated for $C_{27}H_{34}N_2O_2$: Theory: C, 77.48; H, 8.19; N, 6.69. Found: C, 77.64; H, 8.40; N, 6.91.

EXAMPLE 3

1-(3-(3,4-dimethylphenoxy)prop-1-yl)-4-hydroxy-4-(quinolin-3-yl)piperidine

Beginning with 0.218 gm (1.1 mMol) 3-chloropropyl 3,4-dimethylphenyl ether and 0.250 gm (1.1 mMol) 4-hydroxy-4-(quinolin-3-yl)piperidine, 0.114 gm (27%) of the title compound were recovered as a white solid.

MS(m/e): 391(M+1); Calculated for $C_{25}H_{30}N_2O_2$-0.25 $H_2O$: Theory: C, 76.01; H, 7.85; N, 7.15. Found: C, 75.96; H, 7.57; N, 7.07.

EXAMPLE 4

1-(3-(2,4-dimethylphenoxy)prop-1-yl)-4-hydroxy-4-(quinolin-3-yl)piperidine

Beginning with 0.235 gm (1.2 mMol) 3-chloropropyl 2,4-dimethylphenyl ether and 0.270 gm (1.2 mMol) 4-hydroxy-4-(quinolin-3-yl)piperidine, 0.209 gm (45%) of the title compound were recovered as a white solid.

MS(m/e): 390(M$^+$); Calculated for $C_{25}H_{30}N_2O_2$-0.25 $H_2O$: Theory: C, 76.01; H, 7.85; N, 7.15. Found: C, 76.08; H, 7.56; N, 7.07.

EXAMPLE 5

1-(3-(2,4-dichlorophenoxy)prop-1-yl)-4-hydroxy-4-(quinolin-3-yl)piperidine oxalate Beginning with 0.314 gm (1.3 mMol) 3-chloropropyl 2,4-dichlorophenyl ether and 0.300 gm (1.3 mMol) 4-hydroxy-4-(quinolin-3-yl)piperidine, 0.277 gm (49%) of 1-(3-(2,4-dichlorophenoxy)prop-1-yl)-4-hydroxy-4-(quinolin-3-yl)piperidine were recovered as a white, waxy solid. A portion was converted to the oxalate salt.

m.p.=118° C.; Ms (m/e): 430 (M$^+$); Calculated for $C_{23}H_{24}N_2O_2Cl_2 \cdot C_2H_2O_4$: Theory: C, 57.59; H, 5.02; N, 5.37. Found: C, 57.83; H, 5.07; N, 5.49.

EXAMPLE 6

1-(3-(2,6-dimethoxyphenoxy)prop-1-yl)-4-hydroxy-4-(quinolin-3-yl)piperidine oxalate Beginning with 0.303 gm (1.3 mMol) 3-chloropropyl 2,4-dichlorophenyl ether and 0.300 gm (1.3 mMol) 4-hydroxy-4-(quinolin-3-yl)piperidine, 0.318 gm (57%) of 1-(3-(2,6-dimethoxyphenoxy)prop-1-yl)-4-hydroxy-4-(quinolin-3-yl)piperidine were recovered as a white foam. A portion was converted to the oxalate salt.

m.p.=102° C.; MS(m/e): 422(M$^+$).

EXAMPLE 7

1-(3-(indol-4-yloxy)prop-1-yl)-4-hydroxy-4-(quinolin-3-yl)piperidine

Beginning with 0.253 gm (1.2 mMol) 3-chloropropyl indol-4-yl ether and 0.275 gm (1.2 mMol) 4-hydroxy-4-(quinolin-3-yl)piperidine, 0.253 gm (52%) of the title compound were recovered as a white solid.

MS(m/e): 401(M$^+$); Calculated for $C_{25}H_{27}N_3O_2$: Theory: C, 74.79; H, 6.78; N, 10.47. Found: C, 74.66; H, 6.87; N, 10.43.

EXAMPLE 8

1-(3-(indol-4-yloxy)prop-1-yl)-4-hydroxy-4-(isoquinolin-4-yl)piperidine

Beginning with 0.184 gm (0.88 mMol) 3-chloropropyl indol-4-yl ether and 0.200 gm (0.88 mMol) 4-hydroxy-4-(isoquinolin-4-yl)piperidine, 0.169 gm (48%) of the title compound were recovered as a light yellow solid.

MS(m/e): 401(M$^+$); Calculated for $C_{25}H_{27}N_3O_2$: Theory: C, 74.79; H, 6.78; N, 10.47. Found: C, 74.51; H, 6.76; N, 10.34.

EXAMPLE 9

1-(3-(indol-5-yloxy)prop-1-yl)-4-hydroxy-4-(quinolin-3-yl)piperidine

Beginning with 0.275 gm (1.3 mMol) 3-chloropropyl indol-5-yl ether and 0.300 gm (1.3 mMol) 4-hydroxy-4-(quinolin-3-yl)piperidine, 0.238 gm (45%) of the title compound were recovered as an off-white solid.

MS(m/e): 401 (M$^+$); Calculated for $C_{25}H_{27}N_3O_2$: Theory: C, 74.79; H, 6.78; N, 10.47. Found: C, 74.77; H, 6.73; N, 10.36.

EXAMPLE 10

1-(3-(2,2-dimethyl-2,3-dihydrobenzofur-7-yloxy)prop-1-yl)-4-hydroxy-4-(quinolin-3-yl)piperidine Beginning with 0.316 gm (1.3 mMol) 3-chloropropyl 2,2-dimethyl-2,3-dihydrobenzofur-7-yl ether and 0.300 gm (1.3 mMol) 4-hydroxy-4-(quinolin-3-yl)piperidine, 0.262 gm (46%) of the title compound were recovered as a white solid.

MS(m/e): 432(M$^+$); Calculated for $C_{27}H_{32}N_2O_3$: Theory: C, 74.97; H, 7.46; N, 6.48. Found: C, 75.25; H, 7.73; N, 6.68.

EXAMPLE 11

1-(3-(indol-4-yloxy)prop-1-yl)-4-(isoquinolin-4-yl)piperidine oxalate

Beginning with 0.109 gm (0.5 mMol) 3-chloropropyl indol-4-yl ether and 0.110 gm (0.5 mMol) 4-(isoquinolin-4-yl)piperidine, 0.112 gm (56%) of 1-(3-(indol-4-yloxy)prop-1-yl)-4-(isoquinolin-4-yl)piperidine were recovered as an off-white solid. A portion was converted to the oxalate salt.

m.p.=99° C.; MS(m/e): 385(M$^+$); Calculated for $C_{25}H_{27}N_3O \cdot C_2H_2O_4 \cdot 0.75\ H_2O$: Theory: C, 66.32; H, 6.24; N, 8.59. Found: C, 66.54; H, 6.23; N, 8.88.

EXAMPLE 12

1-(3-(indol-4-yloxy)prop-1-yl)-4-(quinolin-3-yl)piperidine

Beginning with 0.175 gm (0.83 mMol) 3-chloropropyl indol-4-yl ether and 0.177 gm (0.83 mMol) 4-(quinolin-3-yl)piperidine, 0.217 gm (68%) of the title compound were recovered as an off-white solid.

MS(m/e): 385(M$^+$); Calculated for $C_{25}H_{27}N_3O$: Theory: C, 77.89; H, 7.06; N, 10.90. Found: C, 77.66; H, 7.07; N, 10.68.

EXAMPLE 13

1-((2R,S)-hydroxy-3-phenoxyprop-1-yl)-4-hydroxy-4-(quinolin-3-yl)piperidine

A mixture of 0.18 mL (1.3 mMol) (2R,S)-glycidyl phenyl ether and 0.300 gm (1.3 mMol) 4-hydroxy- 4-(quinolin-3-yl)piperidine in 10 mL methanol was heated at reflux for 18 hours. The reaction mixture was then cooled to room temperature and partitioned between ethyl acetate and 2N sodium hydroxide. The phases were separated and the aqueous phase extracted well with ethyl acetate. The combined organic phases were washed with saturated aqueous sodium chloride, dried over sodium sulfate and concentrated under reduced pressure. The residue was subjected to flash silica gel chromatography, eluting with 25:1 dichloromethane:methanol. Fractions containing product were combined and concentrated under reduced pressure to provide 0.209 gm (42%) of the title compound as a tan, waxy solid.

Ms(m/e): 378(M$^+$); Calculated for $C_{23}H_{26}N_2O_3$: Theory: C, 72.99; H, 6.92; N, 7.40. Found: C, 72.53; H, 6.78; N, 7.33.

The compounds of Examples 14–60 were prepared by the procedure described in detail in Example 13.

EXAMPLE 14

1-((2S)-hydroxy-3-(4-methylphenoxy)prop-1-yl)-4-hydroxy-4-(quinolin-3-yl)piperidine Beginning with 0.108 gm (0.7 mMol) (S)-glycidyl 4-methylphenyl ether and 0.150 gm (0.7 mMol) 4-hydroxy-4-(quinolin-3-yl)piperidine, 0.175 gm (68%) of the title compound were recovered as a white solid.

MS(m/e): 392(M⁺); Calculated for $C_{24}H_{28}N_2O_3 \cdot 0.5\,H_2O$: Theory: C, 71.80; H, 7.28; N, 6.98. Found: C, 72.01; H, 6.99; N, 7.03.

EXAMPLE 15

1-((2S)-hydroxy-3-(4-ethylphenoxy)prop-1-yl)-4-hydroxy-4-(quinolin-3-yl)piperidine Beginning with 0.117 gm (0.7 mMol) (S)-glycidyl 4-ethylphenyl ether and 0.150 gm (0.7 mMol) 4-hydroxy-4-(quinolin-3-yl)piperidine, 0.100 gm (37%) of the title compound were recovered as a waxy solid. This material was converted to the oxalate salt.

m.p.=76° C.; MS(m/e): 406(M⁺); Calculated for $C_{25}H_{30}N_2O_3 \cdot C_2H_2O_4$: Theory: C, 65.31; H, 6.50; N, 5.64. Found: C, 65.23; H, 6.46; N, 5.56.

EXAMPLE 16

1-((2S)-hydroxy-3-(4-isopropylphenoxy)prop-1-yl)-4-hydroxy-4-(quinolin-3-yl)piperidine Beginning with 0.126 gm (0.7 mMol) (S)-glycidyl 4-isopropylphenyl ether and 0.150 gm (0.7 mMol) 4-hydroxy-4-(quinolin-3-yl)piperidine, 0.121 gm (44%) of the title compound were recovered as a light yellow solid. This material was converted to the oxalate salt.

MS(m/e): 421(M+1); Calculated for $C_{25}H_{30}N_2O_3 \cdot C_2H_2O_4 \cdot 0.5\,H_2O$: Theory: C, 64.72; H, 6.79; N, 5.39. Found: C, 64.61; H, 6.75; N, 5.39.

EXAMPLE 17

1-((2S)-hydroxy-3-(4-tert-butylphenoxy)prop-1-yl)-4-hydroxy-4-(quinolin-3-yl)piperidine Beginning with 0.136 gm (0.7 mMol) (S)-glycidyl 4-tert-butylphenyl ether and 0.150 gm (0.7 mMol) 4-hydroxy-4-(quinolin-3-yl)piperidine, 0.115 gm (40%) of the title compound were recovered as a white foam.

MS(m/e): 434(M⁺); Calculated for $C_{27}H_{34}N_2O_3 \cdot 0.5\,H_2O$: Theory: C, 73.11; H, 7.95; N, 6.32. Found: C, 72.92; H, 7.53; N, 6.48.

EXAMPLE 18

1-((2S)-hydroxy-3-(4-chlorophenoxy)prop-1-yl)-4-hydroxy-4-(quinolin-3-yl)piperidine Beginning with 0.121 gm (0.7 mMol) (S)-glycidyl 4-chlorophenyl ether and 0.150 gm (0.7 mMol) 4-hydroxy-4-(quinolin-3-yl)piperidine, 0.156 gm (58%) of the title compound were recovered as an off-white foam.

Calculated for $C_{23}H_{25}N_2O_3Cl$: Theory: C, 66.90; H, 6.10; N, 6.78. Found: C, 66.73; H, 6.00; N, 6.94. This foam was converted to the oxalate salt. m.p.=81° C.; MS(m/e): 413 (M⁺); Calculated for $C_{23}H_{25}N_2O_3Cl_1 \cdot C_2H_2O_4$: Theory: C, 59.70; H, 5.41; N, 5.57. Found: C, 59.58; H, 5.70; N, 5.28.

EXAMPLE 19

1-((2S)-hydroxy-3-(4-iodophenoxy)prop-1-yl)-4-hydroxy-4-(quinolin-3-yl)piperidine Beginning with 0.181 gm (0.7 mMol) (S)-glycidyl 4-iodo-phenyl ether and 0.150 gm (0.7 mMol) 4-hydroxy-4-(quinolin-3-yl)piperidine, 0.201 gm (61%) of the title compound were recovered as a white solid. This solid was converted to the oxalate salt.

MS(m/e): 504(M⁺); Calculated for $C_{23}H_{25}N_2O_3I \cdot C_2H_2O_4$: Theory: C, 50.52; H, 4.58; N, 4.72. Found: C, 50.40; H, 4.70; N, 4.42.

EXAMPLE 20

1-((2S)-hydroxy-3-(4-trifluoromethylphenoxy)prop-1-yl)-4-hydroxy-4-(quinolin-3-yl)piperidine Beginning with 0.143 gm (0.7 mMol) (S)-glycidyl 4-trifluoromethylphenyl ether and 0.150 gm (0.7 mMol) 4-hydroxy-4-(quinolin-3-yl)piperidine, 0.200 gm (68%) of the title compound were recovered as a white solid.

MS(m/e): 446(M⁺); Calculated for $C_{24}H_{25}N_2O_3F_3 \cdot 0.25\,H_2O$: Theory: C, 63.92; H, 5.70; N, 6.21. Found: C, 63.85; H, 5.58; N, 6.22.

EXAMPLE 21

1-((2S)-hydroxy-3-(2-methoxyphenoxy)prop-1-yl)-4-hydroxy-4-(quinolin-3-yl)piperidine Beginning with 0.118 gm (0.7 mMol) (S)-glycidyl 2-methoxyphenyl ether and 0.150 gm (0.7 mMol) 4-hydroxy-4-(quinolin-3-yl)piperidine, 0.145 gm (54%) of the title compound were recovered as a white foam.

Calculated for $C_{24}H_{28}N_2O_4 \cdot 0.75\,H_2O$: Theory: C, 68.31; H, 7.05; N, 6.64. Found: C, 68.61; H, 6.83; N, 6.56. $[\alpha]_D^{25}$(methanol)=+11.719°; This foam was converted to the oxalate salt. m.p.=182–185° C.; MS(m/e): 408(M⁺); Calculated for $C_{24}H_{28}N_2O_4 \cdot C_2H_2O_4$: Theory: C, 62.64; H, 6.07; N, 5.62. Found: C, 62.51; H, 6.13; N, 5.46. $[\alpha]_D^{25}$(methanol)=−8.741°.

EXAMPLE 22

1-((2S)-hydroxy-3-(3-methoxyphenoxy)prop-1-yl)-4-hydroxy-4-(quinolin-3-yl)piperidine Beginning with 0.118 gm (0.7 mMol) (S)-glycidyl 3-methoxyphenyl ether and 0.150 gm (0.7 mMol) 4-hydroxy-4-(quinolin-3-yl)piperidine, 0.179 gm (67%) of the title compound were recovered as a white foam.

Calculated for $C_{24}H_{28}N_2O_4 \cdot 0.25\,H_2O$: Theory: C, 69.80; H, 6.96; N, 6.78. Found: C, 69.57; H, 6.74; N, 6.92. $[\alpha]_D^{25}$(methanol)=+5.254°; This foam was converted to the oxalate salt. m.p.=79° C.; MS(m/e): 408(M⁺); Calculated for $C_{24}H_{28}N_2O_4 \cdot C_2H_2O_4 \cdot 2H_2O$ Theory: C, 58.42; H, 6.41; N, 5.24. Found: C, 58.45; H, 5.67; N, 5.27. $[\alpha]_D^{25}$(methanol)=−15.444°.

EXAMPLE 23

1-((2S)-hydroxy-3-(4-methoxyphenoxy)prop-1-yl)-4-hydroxy-4-(quinolin-3-yl)piperidine Beginning with 0.118 gm (0.7 mMol) (S)-glycidyl 4-methoxyphenyl ether and 0.150 gm (0.7 mMol) 4-hydroxy-4-(quinolin-3-yl)piperidine, 0.168 gm (63%) of the title compound were recovered as a white waxy solid.

Calculated for $C_{24}H_{28}N_2O_4$: Theory: C, 70.57; H, 6.91; N, 6.86. Found: C, 70.58; H, 7.04; N, 7.01. $[\alpha]_D^{25}$(methanol)=+12.635°; This foam was converted to the oxalate salt. m.p.=63° C.; MS(m/e): 408(M⁺); Calculated for $C_{24}H_{28}N_2O_4 \cdot C_2H_2O_4 \cdot 0.75\,H_2O$: Theory: C, 60.99; H, 6.20; N, 5.47. Found: C, 60.89; H, 6.34; N, 5.47. $[\alpha]_D^{25}$(methanol)=−7.843°.

EXAMPLE 24

1-((2S)-hydroxy-3-(4-trifluoromethoxyphenoxy)prop-1-yl)-4-hydroxy-4-(quinolin-3-yl)piperidine Beginning with 0.154 gm (0.7 mMol) (S)-glycidyl 4-trifluoromethoxyphenyl ether and 0.150 gm (0.7 mMol)

4-hydroxy-4-(quinolin-3-yl)piperidine, 0.207 gm (68%) of the title compound were recovered as a white foam. This foam was converted to the oxalate salt.

MS(m/e): 462(M$^+$); Calculated for $C_{24}H_{28}N_2O_4F_3$: Theory: C, 56.52; H, 4.93; N, 5.07. Found: C, 56.46; H, 4.77; N, 4.86.

EXAMPLE 25

1-((2S)-hydroxy-3-(4-phenoxyphenoxy)prop-1-yl)-4-hydroxy-4-(quinolin-3-yl)piperidine Beginning with 0.169 gm (0.7 mMol) (S)-glycidyl 4-phenoxyphenyl ether and 0.150 gm (0.7 mMol) 4-hydroxy-4-(quinolin-3-yl)piperidine, 0.117 gm (38%) of the title compound were recovered as a light yellow foam. This foam was converted to the oxalate salt.

m.p.=63° C.; MS(m/e): 470(M$^+$); Calculated for $C_{29}H_{30}N_2O_4 \cdot C_2H_2O_4$: Theory: C, 66.42; H, 5.75; N, 5.00. Found: C, 66.23; H, 5.88; N, 5.07.

EXAMPLE 26

1-((2S)-hydroxy-3-(2-methylthiophenoxy)prop-1-yl)-4-hydroxy-4-(quinolin-3-yl)piperidine Beginning with 0.300 gm (1.5 mMol) (S)-glycidyl 2-methylthiophenyl ether and 0.349 gm (1.5 mMol) 4-hydroxy-4-(quinolin-3-yl)piperidine, 0.333 gm (51) of the title compound were recovered as a white solid.

Calculated for $C_{24}H_{28}N_2O_3S$: Theory: C, 67.90; H, 6.65; N, 6.60. Found: C, 68.08; H, 6.70; N, 6.63. $[\alpha]_D^{25}$ (methanol)=−3.984°; This foam was converted to the oxalate salt. m.p.=186–189° C.; MS(m/e): 424(M$^+$); Calculated for $C_{24}H_{28}N_2O_3S \cdot C_2H_2O_4$: Theory: C, 60.69; H, 5.88; N, 5.44. Found: C, 60.69; H, 5.74; N, 5.43. $[\alpha]_D^{25}$ (methanol)=−30.361°.

EXAMPLE 27

1-((2S)-hydroxy-3-(4-methylthiophenoxy)prop-1-yl)-4-hydroxy-4-(quinolin-3-yl)piperidine Beginning with 0.169 gm (0.7 mMol) (S)-glycidyl 4-methylthiophenyl ether and 0.150 gm (0.7 mMol) 4-hydroxy-4-(quinolin-3-yl)piperidine, 0.104 gm (22%) of the title compound were recovered as a white solid. This solid was converted to the oxalate salt.

MS(m/e): 424(M$^+$); Calculated for $C_{24}H_{28}N_2O_3S \cdot C_2H_2O_4$: Theory: C, 60.69; H, 5.88; N, 5.44. Found: C, 60.95; H, 6.07; N, 5.53.

EXAMPLE 28

1-((2S)-hydroxy-3-(2,3-dimethylphenoxy)prop-1-yl)-4-hydroxy-4-(quinolin-3-yl)piperidine Beginning with 0.117 gm (0.7 mMol) (S)-glycidyl 2,3-dimethylphenyl ether and 0.150 gm (0.7 mMol) 4-hydroxy-4-(quinolin-3-yl)piperidine, 0.152 gm (57%) of the title compound were recovered as an off-white solid.

Calculated for $C_{25}H_{30}N_2O_3$: Theory: C, 73.86; H, 7.44; N, 6.89. Found: C, 73.59; H, 7.26; N, 6.90. $[\alpha]_D^{25}$ (methanol)=+5.714°; This solid was converted to the oxalate salt. m.p.=72° C.; MS(m/e): 406(M$^+$); Calculated for $C_{25}H_{30}N_2O_3 \cdot C_2H_2O_4$: Theory: C, 65.31; H, 6.50; N, 5.64. Found: C, 65.13; H, 6.58; N, 5.63. $[\alpha]_D^{25}$(methanol)=−21.016°.

EXAMPLE 29

1-((2S)-hydroxy-3-(3,4-dimethylphenoxy)prop-1-yl)-4-hydroxy-4-(quinolin-3-yl)piperidine Beginning with 0.117 gm (0.7 mMol) (S)-glycidyl 3,4-dimethylphenyl ether and.0.150 gm (0.7 mMol) 4-hydroxy-4-(quinolin-3-yl)piperidine, 0.163 gm (61%) of the title compound were recovered as an off-white solid. Calculated for $C_{25}H_{30}N_2O_3$: Theory: C, 73.86; H, 7.44; N, 6.89. Found: C, 73.64; H, 7.53; N, 6.82. $[\alpha]_D^{25}$ (methanol)=+10.0381°; This solid was converted to the oxalate salt. m.p.=117° C.; MS(m/e): 406(M$^+$); $[\alpha]_D^{25}$ (methanol)=−5.455°.

EXAMPLE 30

1-((2S)-hydroxy-3-(2,4-dimethylphenoxy)prop-1-yl)-4-hydroxy-4-(quinolin-3-yl)piperidine Beginning with 0.180 gm (1.0 mMol) (S)-glycidyl 2,4-dimethylphenyl ether and 0.231 gm (1.0 mMol) 4-hydroxy-4-(quinolin-3-yl)piperidine, 0.318 gm (77%) of the title compound were recovered as a light pink solid.

Calculated for $C_{25}H_{30}N_2O_3$: Theory: C, 73.86; H, 7.44; N, 6.89. Found: C, 73.70; H, 7.28; N, 6.61. $[\alpha]_D^{25}$ (methanol)=+7.38°; This solid was converted to the oxalate salt. m.p.=102° C.; MS(m/e): 406(M$^+$); $[\alpha]_D^{25}$(methanol)=−5.747°.

EXAMPLE 31

1-((2S)-hydroxy-3-(2,4-dichlorophenoxy)prop-1-yl)-4-hydroxy-4-(quinolin-3-yl)piperidine Beginning with 0.144 gm (0.7 mMol) (S)-glycidyl 2,4-dichlorophenyl ether and 0.150 g m (0. 7 mMol) 4-hydroxy-4-(quinolin-3-yl) piperidine, 0.176 gm (60%) of the title compound were recovere d as an off-white solid .

Calculated for $C_{23}H_{24}N_2O_3Cl_2$: Theory: C, 61.75; H, 5.41; N, 6.26. Found: C, 61.50; H, 5.60; N, 6.13. $[\alpha]_D^{25}$ (methanol)=+8.913°; This solid was converted to the oxalate salt. m.p.=86° C.; MS(m/e): 447(M$^+$); $[\alpha]_D^{25}$ (methanol)=−3.521°.

EXAMPLE 32

1-((2S)-hydroxy-3-(2-meth oxy-4-methylphenoxy) prop-1-yl)-4-hydroxy-4-(quinolin-3-yl)piperidine Beginning with 0.091 gm (0.7 mMol) (S)-glycidyl 2-methoxy-4-methylphenyl ether and 0.150 gm (0.7 mMol ) 4-hydroxy-4-(quinolin-3-yl)piperidine, 0.142 gm (59%) of the title compound were recovered as an off-white foam. Calculated for $C_{25}H_{30}N_2O_4 \cdot 0.50 H_2O$: Theory: C, 69.58; H, 7.24; N, 6.49. Found: C, 69.45; H, 7.24; N, 6.43.

This foam was converted to the oxalate salt. m.p.=81° C.; MS(m/e): 422(M$^+$).

EXAMPLE 33

1-((2S)-hydroxy-3-(2-methyl-4-methylthiophenoxy) prop-1-yl) 4-hydroxy-4-(quinolin-3-yl)piperidine Beginning with 0.138 gm (0.7 mMol) (S)-glycidyl 2-methyl-4-methylthiophenyl ether and 0.150 gm (0.7 mMol) 4-hydroxy-4-(quinolin-3-yl)piperidine, 0.184 gm (64%) of the title compound were recovered as a light yellow foam. Calculated for $C_{25}H_{30}N_2O_3S$: Theory: C, 68.46; H, 6.90; N, 6.39. Found: C, 68.19; H, 6.67; N, 6.33.

This foam was converted to the oxalate salt. m.p.=81° C.; MS(m/e): 438(M$^+$); Calculated for $C_{25}H_{30}N_2O_3S \cdot C_2H_2O_4$: Theory: C, 61.35; H, 6.10; N, 5.30. Found: C, 61.55; H, 6.14; N, 5.18.

EXAMPLE 34

1-((2S)-hydroxy-3-(3-methyl-4-acetylphenoxy)prop-1-yl)-4-hydroxy-4-(quinolin-3-yl)piperidine Beginning with 0.135 gm (0.7 mMol) (S)-glycidyl 3-methyl-4-acetylphenyl ether and 0.150 gm (0.7 mMol)

4-hydroxy-4-(quinolin-3-yl)piperidine, 0.147 gm (52%) of the title compound were recovered as an off-white foam.

This foam was converted to the oxalate salt. MS(m/e): 435(M+1); Calculated for $C_{26}H_{30}N_2O_4 \cdot C_2H_2O_4$-0.5 $H_2O$ Theory: C, 63.03; H, 6.23; N, 5.25. Found: C, 62.87; H, 6.02; N, 5.31.

EXAMPLE 35

1-((2S)-hydroxy-3-(2-methyl-4-acetylphenoxy)prop-1-yl)-4-hydroxy-4-(quinolin-3-yl)piperidine Beginning with 0.135 gm (0.7 niMol) (S)-glycidyl 2-methyl-4-acetylphenyl ether and 0.150 gm (0.7 mMol) 4-hydroxy-4-(quinolin-3-yl)piperidine, 0.134 gm (49%) of the title compound were recovered as an off-white foam. Calculated for $C_{26}H_{30}N_2O_4$ Theory: C, 71.87; H, 6.96; N, 6.45. Found: C, 71.71; H, 6.86; N, 6.42.

This foam was converted to the oxalate salt. m.p.=90° C.; MS(m/e): 435(M+1).

EXAMPLE 36

1-((2S)-hydroxy-3-(2-benzoyl-4-methylphenoxy) prop-1-yl)-4-hydroxy-4-(quinolin-3-yl)piperidine Beginning with 0.176 gm (0.7 mMol) (S)-glycidyl 2-benzoyl-4-methylphenyl ether and 0.150 gm (0.7 mMol) 4-hydroxy-4-(quinolin-3-yl)piperidine, 0.199 gm (61%) of the title compound were recovered as an off-white foam. Calculated for $C_{31}H_{32}N_2O_4$: Theory: C, 74.98; H, 6.49; N, 5.64. Found: C, 74.82; H, 6.26; N, 5.58.

This foam was converted to the oxalate salt. m.p.=97° C. MS(m/e): 497(M+1); Calculated for $C_{31}H_{32}N_2O_4 \cdot C_2H_2O_4$: Theory: C, 67.57; H, 5.84; N, 4.78. Found: C, 67.76; H, 6.00; N, 4.85.

EXAMPLE 37

1-((2S)-hydroxy-3-(naphth-2-yloxy)prop-1-yl)-4-hydroxy-4-(quinolin-3-yl)piperidine Beginning with 0.132 gm (0.7 mMol) (S)-glycidyl naphth-2-yl ether and 0.150 gm (0.7 mMol) 4-hydroxy-4-(quinolin-3-yl)piperidine, 0.139 gm (49%) of the title compound were recovered as a white solid.

MS(m/e): 428(M+); $[\alpha]_D^{25}$ (methanol)=−5.814°; Calculated for $C_{27}H_{28}N_2O_3$-0.25 $H_2O$ Theory: C, 74.89; H, 6.63; N, 6.47. Found: C, 74.71; H, 6.67; N, 6.37.

EXAMPLE 38

1-((2S)-hydroxy-3-(6-methoxynaph-2-yloxy)prop-1-yl)-4-hydroxy-4-(quinolin-3-yl)piperidine Beginning with 0.151 gm (0.7 mMol) (S)-glycidyl 6-methoxynaphth-2-yl ether and 0.150 gm (0.7 mMol) 4-hydroxy-4-(quinolin-3-yl)piperidine, 0.172 gm (57%) of the title compound were recovered as a white foam. This foam was converted to the oxalate salt.

MS(m/e): 458(M+); Calculated for $C_{28}H_{30}N_2O_4 \cdot C_2H_2O_4$: Theory: C, 65.68; H, 5.88; N, 5.11. Found: C, 65.43; H, 6.10; N, 5.06.

EXAMPLE 39

1-((2S)-hydroxy-3-(indol-4-yloxy)prop-1-yl)-4-hydroxy-4-(quinolin-3-yl)piperidine Beginning with 0.228 gm (1.2 mMol) (S)-glycidyl indol-4-yl ether and 0.275 gm (1.2 mMol) 4-hydroxy-4-(quinolin-3-yl)piperidine, 0.283 gm (56%) of the title compound were recovered as a white solid.

Calculated for $C_{25}H_{27}N_3O_3$: Theory: C, 71.92; H, 6.52; N, 10.06. Found: C, 71.76; H, 6.66; N, 9.99. $[\alpha]_D^{25}$ (methanol)=+13.841°; This solid was converted to the oxalate salt. m.p.=117–120° C.; MS(m/e): 417(M+); $[\alpha]_D^{25}$ (methanol)=−7.018°.

EXAMPLE 40

1-((2S)-hydroxy-3-(indol-5-yloxy)prop-1-yl)-4-hydroxy-4-(quinolin-3-yl)piperidine Beginning with 0.129 gm (0.7 mMol) (S)-glycidyl indol-5-yl ether and 0.156 gm (0.7 mMol) 4-hydroxy-4-(quinolin-3-yl)piperidine, 0.134 gm (47%) of the title compound were recovered as a white solid.

Calculated for $C_{25}H_{27}N_3O_3$: Theory: C, 71.92; H, 6.52; N, 10.06. Found: C, 71.63; H, 6.71; N, 9.85. $[\alpha]_D^{25}$ (methanol)=+7.505°; This solid was converted to the oxalate salt. m.p.=122° C. MS(m/e): 417(M+); Calculated for $C_{25}H_{27}N_3O_3 \cdot C_2H_2O_4$: Theory: C, 63.90; H, 5.76; N, 8.28. Found: C, 63.87; H, 5.76; N, 8.17. $[\alpha]_D^{25}$(methanol)=−6.479°.

EXAMPLE 41

1-((2R)-hydroxy-3-(indol-5-yloxy)prop-1-yl)-4-hydroxy-4-(quinolin-3-yl)piperidine Beginning with 0.335 gm (1.8 mMol) (R)-glycidyl 5-yl ether and 0.404 gm (1.8 mMol) 4-hydroxy- 4-(quinolin-3-yl)piperidine, 0.397 gm (54%) of the title compound were recovered as a white solid.

Calculated for $C_{25}H_{27}N_3O_3$-1.25 $H_2O$: Theory: C, 68.23; H, 6.18; N, 9.54. Found: C, 68.51; H, 6.28; N, 9.44. $[\alpha]_D^{25}$(methanol)=−12.635°; This solid was converted to the oxalate salt. m.p.=99° C.; MS(m/e): 417(M+); Calculated for $C_{25}H_{27}N_3O_3 \cdot C_2H_2O_4$: Theory: C, 63.90; H, 5.76; N, 8.28. Found: C, 64.40; H, 5.82; N, 8.36. $[\alpha]_D^{25}$(methanol)=+8.547°.

EXAMPLE 42

1-((2S)-hydroxy-3-(1-methylindol-4-yloxy)prop-1-yl)-4-hydroxy-4-(quinolin-3-yl)piperidine Beginning with 0.134 gm (0.7 mMol) (S)-glycidyl 1-methylindol-4-yl ether and 0.150 gm (0.7 mMol) 4-hydroxy-4-(quinolin-3-yl)piperidine, 0.217 gm (76%) of the title compound were recovered as an off-white foam.

Calculated for $C_{26}H_{29}N_3O_3$-0.25 $H_2O$: Theory: C, 71.62; H, 6.82; N, 9.64. Found: C, 71.76; H, 6.82; N, 9.72. $[\alpha]_D^{25}$ (methanol)=+22.414°; This foam was converted to the oxalate salt. m.p.=86° C.; MS(m/e): 431(M+); Calculated for $C_{26}H_{29}N_3O_3 \cdot C_2H_2O_4$: Theory: C, 64.48; H, 5.99; N, 8.06. Found: C, 64.21; H, 5.89; N, 7.95. $[\alpha]_D^{25}$ (methanol)=−5.367°.

EXAMPLE 43

1-((2S)-hydroxy-3-(2-methylindol-4-yloxy)prop-1-yl)-4-hydroxy-4-(quinolin-3-yl)piperidine Beginning with 0.134 gm (0.7 mMol) (S)-glycidyl 2-methylindol-4-yl ether and 0.150 gm (0.7 mMol) 4-hydroxy-4-(quinolin-3-yl)piperidine, 0.198 gm (68%) of the title compound were recovered as an off-white foam.

Calculated for $C_{26}H_{29}N_3O_3$-0.25 $H_2O$: Theory: C, 71.62; H, 6.82; N, 9.64. Found: C, 71.35; H, 6.60; N, 9.36. $[\alpha]_D^{25}$ (methanol)=+3.766°; This foam was converted to the oxalate salt. m.p.=117° C. MS(m/e): 431(M⁺); Calculated for $C_{26}H_{29}N_3O_3$-$C_2H_2O_4$: Theory: C, 64.48; H, 5.99; N, 8.06. Found: C, 64.33; H, 5.95; N, 8.06. $[\alpha]_D^{25}$ (methanol)=−9.96°.

EXAMPLE 44

1-((2S)-hydroxy-3-(benzofur-4-yloxy)prop-1-yl)-4-hydroxy-4-(quinolin-3-yl)piperidine Beginning with 0.094 gm (0.5 mMol) (S)-glycidyl benzofur-4-yl ether and 0.113 gm (0.5 mMol) 4-hydroxy-4-(quinolin-3-yl)piperidine, 0.088 gm (43%) of the title compound were recovered as an off-white foam. This foam was converted to the oxalate salt.

MS(m/e): 419(M+1); Calculated for $C_{25}H_{26}N_2O_4$-$C_2H_2O_4$: Theory: C, 63.77; H, 5.55; N, 5.51. Found: C, 63.79; H, 5.66; N, 5.54.

EXAMPLE 45

1-((2S)-hydroxy-3-(benzothien-4-yloxy)prop-1-yl)-4-hydroxy-4-(quinolin-3-yl)piperidine Beginning with 0.090 gm (0.4 mMol) (S)-glycidyl benzothien-4-yl ether and 0.100 gm (0.4 mMol) 4-hydroxy-4-(quinolin-3-yl)piperidine, 0.139 gm (73%) of the title compound were recovered as an off-white foam. This foam was converted to the oxalate salt.

MS(m/e): 434(M⁺); Calculated for $C_{25}H_{26}N_2O_3S$-$C_2H_2O_4$: Theory: C, 61.82; H, 5.38; N, 5.34. Found: C, 61.86; H, 5.21; N, 5.04.

EXAMPLE 46

1-((2S)-hydroxy-3-(2-methylbenzothiazol-5-yloxy)prop-1-yl)-4-hydroxy-4-(quinolin-3-yl)piperidine Beginning with 0.145 gm (0.7 mMol) (S)-glycidyl 2-methylbenzothiazol-5-yl ether and 0.150 gm (0.7 mMol) 4-hydroxy-4-(quinolin-3-yl)piperidine, 0.181 gm (61%) of the title compound were recovered as an off-white foam.

Calculated for $C_{25}H_{27}N_3O_3S$: Theory: C, 71.62; H, 6.82; N, 9.64. Found: C, 71.76; H, 6.82; N, 9.72. $[\alpha]_D^{25}$ (methanol)=+22.414°; This foam was converted to the oxalate salt. m.p.=86° C.; MS(m/e): 431(M⁺); Calculated for $C_{26}H_{29}N_3O_3$-$C_2H_2O_4$: Theory: C, 64.48; H, 5.99; N, 8.06. Found: C, 64.21; H, 5.89; N, 7.95. $[\alpha]_D^{25}$ (methanol)=−5.367°.

EXAMPLE 47

1-((2S)-hydroxy-3-(indan-4-yloxy)prop-1-yl)-4-hydroxy-4-(quinolin-3-yl)piperidine Beginning with 0.150 gm (0.8 mMol) (S)-glycidyl indol-4-yl ether and 0.180 gm (0.8 mMol) 4-hydroxy-4-(quinolin-3-yl)piperidine, 0.202 gm (61t) of the title compound were recovered as a white foam.

Calculated for $C_{26}H_{30}N_2O_3$-0.25 $H_2O$: Theory: C, 73.82; H, 7.15; N, 6.62. Found: C, 73.66; H, 7.11; N, 6.92. $[\alpha]_D^{25}$ (methanol)=+9.158°; This foam was converted to the oxalate salt. m.p.=85° C.; MS(m/e): 418(M⁺); $[\alpha]_D^{25}$ (methanol)=−5.254°;

EXAMPLE 48

1-((2S)-hydroxy-3-(indan-5-yloxy)prop-1-yl)-4-hydroxy-4-(quinolin-3-yl)piperidine Beginning with 0.125 gm (0.7 mMol) (S)-glycidyl indol-5-yl ether and 0.150 gm (0.7 mMol) 4-hydroxy- 4-(quinolin-3-yl)piperidine, 0.160 gm (58%) of the title compound were recovered as a white solid.

Calculated for $C_{26}H_{30}N_2O_3$-0.50 $H_2O$: Theory: C, 73.04; H, 7.31; N, 6.55. Found: C, 72.68; H, 7.13; N, 6.74. $[\alpha]_D^{25}$(methanol)=−205.31°; This solid was converted to the oxalate salt. m.p.=66° C.; MS(m/e): 418(M⁺); $[\alpha]_D^{25}$ (methanol)=−3.472°;

EXAMPLE 49

1-((2S)-hydroxy-3-(7-methylindan-4-yloxy)prop-1-yl)-4-hydroxy-4-(quinolin-3-yl)piperidine Beginning with 0.134 gm (0.7 mMol) (S)-glycidyl 7-methylindan-4-yl ether and 0.150 gm (0.7 mMol) 4-hydroxy-4-(quinolin-3-yl)piperidine, 0.165 gm (58%) of the title compound were recovered as a light tan foam.

Calculated for $C_{27}H_{32}N_2O_3$: Theory: C, 74.97; H, 7.46; N, 6.48. Found: C, 74.81; H, 7.43; N, 6.18. $[\alpha]_D^{-}$ (methanol)=+3.61°; This foam was converted to the oxalate salt. m.p.=94° C.; MS(m/e): 432(M⁺); Calculated for $C_{26}H_{29}N_3O_3$-$C_2H_2O_4$-0.25 $H_2O$: Theory: C, 66.08; H, 6.60; N, 5.31. Found: C, 65.87; H, 6.02; N, 5.46. $[\alpha]_D^{25}$ (methanol)=−9.058°.

EXAMPLE 50

1-((2S)-hydroxy-3-(1,2,3,4-tetrahydronaphth-6-yloxy)prop-1-yl)-4-hydroxy-4-(quinolin-3-yl) piperidine Beginning with 0.134 gm (0.7 mMol) (S)-glycidyl 1,2,3,4-tetrahydronaphth-6-yl ether and 0.150 gm (0.7 mMol) 4-hydroxy-4-(quinolin-3-yl)piperidine, 0.109 gm (38%) of the title compound were recovered as a white foam. This foam was converted to the oxalate salt.

MS(m/e): 433(M+1); Calculated for $C_{27}H_{32}N_2O_3$-$C_2H_2O_4$: Theory: C, 66.65; H, 6.56; N, 5.36. Found: C, 66.51; H, 6.49; N, 5.64.

EXAMPLE 51

1-((2S)-hydroxy-3-(quinolin-6-yloxy)prop-1-yl)-4-hydroxy-4-(quinolin-3-yl)piperidine Beginning with 0.132 gm (0.7 mMol) (S)-glycidyl quinolin-6-yl ether and 0.150 gm (0.7 mMol) 4-hydroxy-4-(quinolin-3-yl)piperidine, 0.182 gm (65%) of the title compound were recovered as a white solid.

Calculated for $C_{26}H_{27}N_3O_3$-1.5 $H_2O$: Theory: C, 68.40; H, 6.62; N, 9.20. Found: C, 68.68; H, 6.17; N, 9.22. $[\alpha]_D^{25}$(methanol)=−24.39°; This solid was converted to the oxalate salt. m.p.=91° C.; MS(m/e): 430(M+1); Calculated for $C_{26}H_{27}N_3O_3$-$C_2H_2O_4$-$H_2O$: Theory: C, 62.56; H, 5.81; N, 7.82. Found: C, 62.66; H, 5.81; N, 7.58. $[\alpha]_D^{25}$ (methanol)=−5.367°.

EXAMPLE 52

1-((2S)-hydroxy-3-(quinolin-7-yloxy)prop-1-yl)-4-hydroxy-4-(quinolin-3-yl)piperidine Beginning with 0.132 gm (0.7 mMol) (S)-glycidyl quinolin-7-yl ether and 0.150 gm (0.7 mMol) 4-hydroxy-4-(quinolin-3-yl)piperidine, 0.199 gm (71%) of the title compound were recovered as an off-white foam. This foam was converted to the oxalate salt.

MS(m/e): 430(M+1); Calculated for $C_{26}H_{27}N_3O_3$-$C_2H_2O_4$-$H_2O$: Theory: C, 62.56; H, 5.81; N, 7.82. Found: C, 62.76; H, 5.75; N, 7.53.

EXAMPLE 53

1-((2S)-hydroxy-3-(julolidin-7-yloxy)prop-1-yl)-4-hydroxy-4-(quinolin-3-yl)piperidine Beginning with 0.134 gm (0.5 mMol) (S)-glycidyl julolidin-7-yl ether and 0.125 gm (0.5 mMol) 4-hydroxy-4-(quinolin-3-yl)piperidine, 0.159 gm (61%) of the title compound were recovered as a light tan foam.

Calculated for $C_{29}H_{35}N_3O_3$-0.5 $H_2O$: Theory: C, 72.85; H, 7.48; N, 8.79. Found: C, 72.50; H, 7.15; N, 8.52. $[\alpha]_D^{25}$ (methanol)=+7.59°; This foam was converted to the oxalate salt. m.p.=84° C.; MS(m/e): 473(M$^+$); $[\alpha]_D^{25}$ (methanol)=−9.728°.

EXAMPLE 54

1-((2S)-hydroxy-3-(dibenzofur-3-yloxy)prop-1-yl)-4-hydroxy-4-(quinolin-3-yl)piperidine Beginning with 0.202 gm (0.8 mMol) (S)-glycidyl dibenzofur-3-yl ether and 0.192 gm (0.8 mMol) 4-hydroxy-4-(quinolin-3-yl)piperidine, 0.133 gm (34%) of the title compound were recovered as an off-white foam.

Calculated for $C_{29}H_{28}N_2O_4$-0.5 $H_2O$: Theory: C, 72.94; H, 6.12; N, 5.87. Found: C, 73.01; H, 6.01; N, 5.87. This foam was converted to the oxalate salt. m.p.=92° C.; MS(m/e): 468(M$^+$); Calculated for $C_{29}H_{28}N_2O_4$-$C_2H_2O_4$-0.75 $H_2O$: Theory: C, 65.08; H, 5.55; N, 4.90. Found: C, 65.15; H, 5.59; N, 4.90.

EXAMPLE 55

1-((2S)-hydroxy-3-(carbazol-2-yloxy)prop-1-yl)-4-hydroxy-4-(quinolin-3-yl)piperidine Beginning with 0.157 gm (0.7 mMol) (S)-glycidyl carbazol-2-yl ether and 0.150 gm (0.7 mMol) 4-hydroxy-4-(quinolin-3-yl)piperidine, 0.034 gm (11%) of the title compound were recovered as a light tan solid.

MS(m/e): 467(M$^+$).

EXAMPLE 56

1-((2S)-hydroxy-3-(indol-4-yloxy)prop-1-yl)-4-hydroxy-4-(isoquinolin-4-yl)piperidine Beginning with 0.166 gm (0.88 mMol) (S)-glycidyl indol-4-yl ether and 0.200 gm (0.88 mMol) 4-hydroxy-4-(isoquino-lin-4-yl)piperidine, 0.125 gm (34%) of the title compound were recovered as a light yellow solid.

Calculated for $C_{25}H_{27}N_3O_3$-0.25 $H_2O$: Theory: C, 71.15; H, 6.45; N, 9.96. Found: C, 70.84; H, 6.55; N, 9.43. $[\alpha]_D^{25}$ (methanol)=−7.233°; This solid was converted to the oxalate salt. m.p.=123° C.; MS(m/e): 417(M$^+$); Calculated for $C_{25}H_{27}N_3O_3$-$C_2H_2O_4$-$H_2O$: Theory: C, 61.70; H, 5.56; N, 7.99. Found: C, 61.87; H, 5.55; N, 7.63. $[\alpha]_D^{25}$ (methanol)=−18.382°.

EXAMPLE 57

1-((2S)-hydroxy-3-(indol-4-yloxy)prop-1-yl)-4-(pyridin-3-yl)piperidine

Beginning with 0.152 gm (0.8 mMol) (S)-glycidyl indol-4-yl ether and 0.130 gm (0.8 mMol) 4-(pyridin-3-yl)piperidine, 0.147 gm (52%) of the title compound were recovered as an off-white solid.

Calculated for $C_{21}H_{25}N_3O_2$-0.5 $H_2O$: Theory: C, 69.98; H, 6.99; N, 11.66. Found: C, 70.18; H, 6.89; N, 11.44. $[\alpha]_D^{25}$(methanol)=+12.195°; This solid was converted to the oxalate salt. m.p.=77° C. MS(m/e): 351(M$^+$); $[\alpha]_D^{25}$ (methanol)=−5.988°.

EXAMPLE 58

1-((2S)-hydroxy-3-(indol-4-yloxy)prop-1-yl)-4-(quinolin-3-yl)piperidine

Beginning with 0.133 gm (0.7 mMol) (S)-glycidyl indol-4-yl ether and 0.149 gm (0.7 mMol) 4-(quinolin- 3-yl)piperidine, 0.133 gm (40%) of the title compound were recovered as an off-white solid.

Calculated for $C_{25}H_{27}N_3O_2$-0.25 $H_2O$: Theory: C, 73.96; H, 6.83; N, 10.35. Found: C, 73.72; H, 6.58; N, 10.16. $[\alpha]_D^{25}$ (methanol)=+3.876°; This solid was converted to the oxalate salt. m.p.=124° C.; MS(m/e): 401(M$^+$); $[\alpha]_D^{25}$ (methanol)=−7.207°.

EXAMPLE 59

1-((2S)-hydroxy-3-(indol-4-yloxy)prop-1-yl)-4-(isoquinolin-4-yl)piperidine

Beginning with 0.083 gm (0.4 mMol) (S)-glycidyl indol-4-yl ether and 0.093 gm (0.4 mMol) 4-(isoquinolin-4-yl)piperidine, 0.072 gm (41%) of the title compound were recovered as an off-white solid. This solid was converted to the oxalate salt.

m.p.=118° C.; MS(m/e): 401(M$^+$); Calculated for $C_{25}H_{27}N_3O_2$-$C_2H_2O_4$-$H_2O$: Theory: C, 63.64; H, 5.74; N, 8.25. Found: C, 63.77; H, 5.62; N, 8.25. $[\alpha]_D^{25}$ (methanol)=−15.2381°.

EXAMPLE 60

1-((2S)-hydroxy-3-(indol-4-yloxy)prop-1-yl)-4-(quinoxalin-2-yl)piperidine

Beginning with 0.108 gm (0.6 mMol) (S)-glycidyl indol-4-yl ether and 0.122 gm (0.6 mMol) 4-(quinoxalin-2-yl)piperidine, 0.137 gm (60%) of the title compound were recovered as a light tan foam. This foam was converted to the oxalate salt.

MS(m/e): 402(M$^+$); Calculated for $C_{24}H_{26}N_4O_2$-$C_2H_2O_4$: Theory: C, 63.40; H, 5.73; N, 11.38. Found: C, 63.30; H, 5.85; N, 11.15.

The ability of the compounds of this invention to bind to the 5-HT$_{1F}$ receptor subtype was measured essentially as described in N. Adham, et al., *Proceedings of the National Academy of Sciences (USA)*, 90, 408–412 (1993).

Membrane Preparation:

Membranes were prepared from transfected Ltk- cells which were grown to 100% confluency. The cells were washed twice with phosphate-buffered saline, scraped from the culture dishes into 5 mL of ice-cold phosphate-buffered saline, and centrifuged at 200×g for 5 minutes at 4° C. The pellet was resuspended in 2.5 mL of ice-cold Tris buffer (20 mM Tris HCl, pH=7.4 at 23° C., 5 mM EDTA) and homogenized with a Wheaton tissue grinder. The lysate was subsequently centrifuged at 200×g for 5 minutes at 4° C. to pellet large fragments which were discarded. The supernatant was collected and centrifuged at 40,000×g for 20 minutes at 4° C. The pellet resulting from this centrifugation was washed once in ice-cold Tris wash buffer and resuspended in a final buffer containing 50 mM Tris HCl and 0.5 mM EDTA, pH=7.4 at 23° C. Membrane preparations were kept on ice and utilized within two hours for the radioligand binding assays. Protein concentrations were determined by the method of Bradford (*Anal. Biochem.*, 72, 248–254 (1976)).

Radioligand Binding:

[$^3$H-5-HT] binding was performed using slight modifications of the 5-HT$_{1D}$ assay conditions reported by Herrick-Davis and Titeler (*J. Neurochem.*, 50, 1624–1631 (1988)) with the omission of masking ligands. Radioligand binding studies were achieved at 37° C. in a total volume of 250 mL of buffer (50 mM Tris, 10 mM MgCl$_2$, 0.2 mM EDTA, 10 mM pargyline, 0.1% ascorbate, pH=7.4 at 37° C.) in 96 well microtiter plates. Saturation studies were conducted using [$^3$H]5-HT at 12 different concentrations ranging from 0.5 nM to 100 nM. Displacement studies were performed using 4.5–5.5 nM [$^3$H]5-HT. The binding profile of drugs in competition experiments was accomplished using 10–12 concentrations of compound. Incubation times were 30 minutes for both saturation and displacement studies based upon initial investigations which determined equilibrium binding conditions. Nonspecific binding was defined in the presence of 10 mM 5-HT. Binding was initiated by the addition of 50 mL membrane homogenates (10–20 $\mu$g). The reaction was terminated by rapid filtration through pre-soaked (0.5% poylethyleneimine) filters using 48R Cell Brandel Harvester (Gaithersburg, Md.). Subsequently, filters were washed for 5 seconds with ice cold buffer (50 mM Tris HCl, pH=7.4 at 4° C.), dried and placed into vials containing 2.5 mL Readi-Safe (Beckman, Fullerton, Calif.) and radioactivity was measured using a Beckman LS 5000TA liquid scintillation counter. The efficiency of counting of [$^3$H]5-HT averaged between 45–50%. Binding data was analyzed by computer-assisted nonlinear regression analysis (Accufit and Accucomp, Lunden Software, Chagrin Falls, Ohio). IC$_{50}$ values were converted to K$_i$ values using the Cheng-Prusoff equation (*Biochem. Pharmacol.*, 22, 3099–3108 (1973). All experiments were performed in triplicate. All of the compounds of the invention exemplified exhibited an IC$_{50}$ at the 5-HT$_{1F}$ receptor of at least 5 $\mu$mol.

As was reported by R.L. Weinshank, et al., WO93/14201, the 5-HT$_{1F}$ receptor is functionally coupled to a G-protein as measured by the ability of serotonin and serotonergic drugs to inhibit forskolin stimulated cAMP production in NIH$_3$T3 cells transfected with the 5-HT$_{1F}$ receptor. Agonist activation of G-protein-coupled receptors also results in the release of GDP from the a-subunit of the G protein and the subsequent binding of GTP. The binding of the stable analog [$^{35}$S]GTP$\gamma$S is an indicator of this receptor activation. In vitro 5-HT$_1$F receptor activation, as measured by [$^{35}$S] GTP$\gamma$S binding, was carried out essentially as described by Wainscott, et al., *European Journal of Pharmacology*, 352, 117–124 (1998).

Membrane Preparation

Mouse LM(tk–)cells stably transfected with the human 5-HT$_{1F}$ receptor and grown in suspension were harvested by centrifugation, resuspended in 50 mM Tris-HCl, pH 7.4, in aliquots of 2×10$^8$ cells and frozen at –70° C. until the day of the assay. On the assay day, an aliquot of cells was thawed, resuspended in 35 mL of 50 mM Tris-HCl, pH 7.4, and centrifuged at 39,800×g for 10 minutes at 4° C. The resulting pellet was resuspended in 50 mM Tris-HCl, pH 7.4, incubated for 10 minutes at 37° C. and centrifuged at 39,800×g for 10 minutes at 4° C. The pellet was resuspended and centrifuged once more, with the final pellet being resuspended in 4 mM MgCl$_2$, 160 mM NaCl, 0.267 mM EGTA, 67 mM Tris-HCl, pH 7.4, such that a 200 mL aliquot contained contained approximately 15–25 mg protein.

[$^{35}$S]GTP$\gamma$S Binding

The assay was modified from published conditions (Sim et al., *Proc. Natl. Acad. Sci. USA*, 92, 7242–7246 (1995); Thomas et al., *J. Rec. Signal Transduct. Res.*, 15, 199–211 (1995)). Two versions of the assay, one using vacuum filtration (Wainscott et al., *Eur J. Pharmacol.*, 352, 117–124 (1998)) and one using a scintillation proximity assay, have been developed for the determination of the potency and intrinsic activity (efficacy) of 5-HT$_{1F}$ ligands.

[$^{35}$S]GTP$\gamma$S Binding Using Vacuum Filtration

Incubations were performed in a total volume of 800 $\mu$l. Test compounds in water (glacial acetic acid and/or dimethyl sufoxide [DMSO] may have been used to aid in solubilizing some compounds), 200 $\mu$l, were added to 400 $\mu$l of Tris-HCl, pH 7.4, containing MgCl$_2$, NaCl, EGTA, GDP and [$^{35}$S] GTP$\gamma$S. Membrane homogenate (200 $\mu$l) was added and the tubes were incubated for 30 min at 37° C. The final concentrations of MgCl$_2$, NaCl, EGTA, GDP, [$^{35}$S]GTP$\gamma$S and Tris were 3 mM, 120 mM, 0.2 mM, 10 $\mu$M, 0.1 nM and 50 mM, respectively. For experiments examining the inhibition of 5-HT stimulated [$^{35}$S]GTP$\gamma$S binding, the final concentration of 5-HT was 1 $\mu$M. Using a Brandel cell harvester (model MB-48R, Brandel, Gaithersburg, Md.), the incubations were terminated by vacuum filtration through Whatman GF/B filters which had been wetted with water or 20 mM Na$_4$P$_2$O$_7$ and pre-cooled with 4 ml of ice-cold 50 mM Tris-HCl, pH 7.4. The filters were then rapidly washed with 4 ml of ice-cold 50 mM Tris-HCl, pH 7.4. The amount of [$^{35}$S]GTP$\gamma$S captured on the filters was determined by liquid scintillation spectrometry.

[$^{35}$S]GTP$\gamma$S Binding Using a Scintillation Proximity Assay

Incubations were performed in a total volume of 200 $\mu$l in 96 well assay plates. [$^{35}$S]GTP$\gamma$S and guanosine-5'-diphosphate in assay buffer (MgCl$_2$, NaCl, EGTA in Tris-HCl, pH 7.4), 50 $\mu$l, were added to 50 $\mu$l of test compounds dissolved in water (glacial acetic acid and/or dimethyl sufoxide [DMSO] may have been used to aid in solubilizing some compounds). Wheat Germ Agglutinin (WGA) beads (Amersham Life Sciences, Inc., Arlington Heights, Ill.) for scintillation proximity assay (SPA), in assay buffer (20, 25 or 50 $\mu$l) were then added. Membrane homogenate (80, 75 or 50 $\mu$l) was added and the plates were covered with sealing tape (Wallac, Inc., Gaithersburg, Md.), and allowed to incubate at room temperature for 2 hr. The final concentrations of MgCl$_2$, NaCl, EGTA, GDP, [$^{35}$S]GTP$\gamma$S and Tris were 3 mM, 120 mM, 0.2 mM, 10 $\mu$M, 0.25 nM and 50 mM, respectively. For experiments examining the inhibition of 5-HT-stimulated [$^{35}$S]GTP$\gamma$S binding, the final concentration of 5-HT was 1 mM. The plates were then centrifuged at approximately 200×g for 10 min at room temperature. The amount of [$^{35}$S]GTP$\gamma$S bound to the membranes, i.e., in close proximity to the WGA SPA beads, was then determined using a Wallac MicroBeta® Trilux Scintillation Counter (Wallac, Inc.).

Data Analysis

Nonlinear regression analysis was performed on the concentration-response curves (generating EC$_{50}$ and E$_{max}$ values for stimulation of [$^{35}$S]GTP$\gamma$S binding or generating IC$_{50}$ and E$_{max}$ values for inhibition of 5-HT-stimulated [$^{35}$S]GTP$\gamma$S binding) using a four parameter logistic equation described by DeLean et al. (De Lean et al., *Mol. Pharmacol.*, 21, 5–16 (1982)). The equation was modified such that the slope was a positive number for stimulation of [$^{35}$S]GTP$\gamma$S binding. Efficacy (E$_{max}$) values, determined by the nonlinear regression analysis, for selected compounds were expressed as the percent of [$^{35}$S]GTP$\gamma$S binding relative to 10 $\mu$M 5-HT which was run as a standard with each concentration-response curve. Efficacy values for compounds run as single point determinations may have also been calculated relative to 10 μM 5-HT-stimulated [$^{35}$S] GTPγS binding, which was run as a standard on each of these assay plates. For inhibition of 5-HT-stimulated [$^{35}$S] GTPγS binding, the IC$_{50}$ values were converted to K$_i$ values using the Cheng-Prusoff equation (Cheng and Prusoff, *Biochem. Pharmacol.*, 22, 3099–3108 (1973)). In addition, the minimum for inhibition of 5-HT-stimulated [$^{35}$S]GTPγS binding also represents a determination of the efficacy (E$_{max}$) value for the tested compounds, calculated as the percent of [$^{35}$S]GTPγS binding relative to 10 μM 5-HT alone as the standard run with each of these curves.

The utility of the compounds of the present invention for the treatment of anxiety disorders was demonstrated by the social interaction assay described by T. J. Sajdyk and A. Shekhar in *The Journal of Pharmacology and Experimental Therapeutics*, 283, 969–977 (1997), a fully validated test of anxiety (S. E. File, *Journal of Neuroscience Methods*, 2, 219–238 (1980)). The procedure for this assay is summarized below.

Animals

All experiments were performed on male Wister rats (Harlan laboratories, 275–300 gm). The rats were individually housed in a temperatu,re controlled room (72° F.) on a 12 hour day/night cycle. The rats were provided food and water ad libitum.

Test Compound

Approximately 40 mg of the test compound was weighed into a 20 mL glass vial. To this solid were added 80 μL of lactic acid (85%). The mixture was sonicated for 2 minutes and then 4 mL of distilled water was added in 1 mL increments. Sonication of this mixture was continued until all of the solid had dissolved. Following sonication, the pH of the mixture was raised by the addition of dilute aqueous sodium hydroxide until the mixture reached a pH of about 5.5.

Protocols

Each rat was weighed and the test compound administered by intraperitoneal injection at 20 mg/kg of body weight. The animals were then placed back in their home cages for 1 hour before the behavioral protocol was initiated.

Experimental anxiety was measured by a social interaction test. The apparatus was a solid wood box (36 inches long×36 inches wide×12 inches high) with an open roof. A video camera was fixed above the social interaction box and all behavioral tests were recorded. During the test session, the rat which received the test compound was placed into the social interaction box with another male Wistar rat which had been housed individually and was unfamiliar to the rat which received the test compound. The rat which received the test compound was observed for 5 minutes. The amount of time that the rat which received test compound spent interacting (i.e. grooming, sniffing, crawling upon) with the other rat was recorded. All tests were performed under lighted conditions. An increase in interaction time represents a decrease in anxiety. Conversely, a decrease in interaction time represents an increase in anxiety.

Statistical Analysis

Social interaction data was analyzed as total interaction time in seconds and the raw scores were compared between baseline and treatment. Statistical analyses were conducted by using a paired students t-test. Statistical significance was accepted at p<0.01.

The compound of Example 37 was tested in this assay and was found to significantly increase social interaction time as compared to baseline at a dose of 20 mg/kg.

The activity of compounds of Formula I in the antagonism of the serotonin 5-HT$_{1F}$ receptor provides a method of treating anxiety disorders comprising administering to a subject in need of such treatment an effective amount of a compound of that formula. Anxiety disorders represent the most prevalent type of psychiatric disorders in the United States. Anxiety disorders include panic disorder, obsessive-compulsive disorder, post-traumatic stress disorder, specific phobia, social phobia, and generalized anxiety disorder. All are characterized by uneasiness, a sense of fearfulness, and distress for no apparent reason. These disorders, if left untreated, reduce the quality of life and productivity of patients suffering from them. In the United States alone, more than 23 million people suffer from anxiety disorders. The cost to society from these disorders is staggering, estimated in 1990 at $46.6 billion in the United States alone in direct and indirect costs.

The diseases to be mentioned here are classified in the Diagnostic and Statistical Manual of Mental Disorders, 4th Version, published by the American Psychiatric Association (DSM). In such cases, the DSM code numbers are supplied below for the convenience of the reader.

| | |
|---|---|
| Panic Disorder Without Agoraphobia | DSM 300.01 |
| Panic Disorder With Agoraphobia | DSM 300.21 |
| Agoraphobia Without History of Panic Disorder | DSM 300.22 |
| Specific Phobia | DSM 300.29 |
| Social Phobia | DSM 300.23 |
| Obsessive-Compulsive Disorder | DSM 300.3 |
| Post-Traumatic Stress Disorder | DSM 309.81 |
| Acute Stress Disorder | DSM 308.3 |
| Generalized Anxiety Disorder | DSM 300.02 |
| Anxiety Disorder Due to a General Medical Condition | DSM 293.84 |
| Substance Induced Anxiety Disorder | |
| Alcohol | DSM 291.89 |
| Amphetamine (or Amphetamine-Like Substance) | DSM 292.89 |
| Caffeine | DSM 292.89 |
| Cannabis | DSM 292.89 |
| Cocaine | DSM 292.89 |
| Hallucinogen | DSM 292.89 |
| Inhalant | DSM 292.89 |
| Phencyclidine (or Phencyclidine-Like Substance) | DSM 292.89 |
| Sedative, Hypnotic, or Anxiolytic | DSM 292.89 |
| Other [Unknown] Substance | DSM 292.89 |
| Anxiety Disorder Not Otherwise Specified | DSM 300.00 |
| Separation Anxiety Disorder | DSM 309.21 |
| Sexual Adversion Disorder | DSM 302.79 |

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See. e.g., REMINGTON'S PHARMACEUTICAL SCIENCES, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

FORMULATION EXAMPLE 1

Hard gelatin capsules containing the following ingredients are prepared:

| Ingredient | Quantity (mg/capsule) |
| --- | --- |
| Compound of Example 24 | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
| --- | --- |
| Compound of Example 25 | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See. e.g., U.S. Pat. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compound(s), and the state of the patient.

We claim:

1. A substituted piperidine of Formula I:

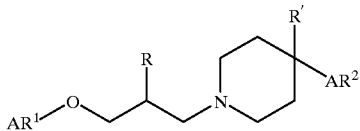

where:
- R and R' are independently hydrogen or hydroxy;
- AR$^1$ is phenyl, naphthyl, quinolinyl, isoquinolinyl, indanyl, 1,2,3,4-tetrahydronaphthyl, indolyl, N-(C$_1$–C$_4$ alkyl)indolyl, benzothiazolyl, benzothienyl, benzofuryl, 2,3-dihydrobenzothienyl, 2,3-dihydrobenzofuryl, julolidinyl, or dibenzofuryl, each optionally substituted with one or two substituents independently selected from the group consisting of C$_1$–C$_6$ alkyl, C$_1$–C$_6$ acyl, benzoyl, C$_1$–C$_6$ alkoxy, phenoxy, C$_1$–C$_6$ alkylthio, trifluoromethyl, trifluoromethoxy, or halo;
- AR$^2$ is pyridin-3-yl, quinolin-3-yl, isoquinolin-4-yl, or quinoxalin-2-yl; or pharmaceutically acceptable acid addition salts thereof.

2. A compound of claim 1 where R is hydroxy.
3. A compound of claim 1 where R' is hydroxy.
4. A compound of claim 1 where R and R' are hydroxy.
5. A compound of claim 1 where AR$^1$ is indolyl.
6. A compound of claim 5 where AR$^1$ is indol-4-yl.
7. A compound of claim 5 where AR$^1$ is indol-5-yl.
8. A compound of claim 5 where AR$^2$ is quinolin-3-yl.
9. A method for decreasing the activation of the 5-HT$_{1F}$ receptor comprising administering to a mammal in need of such treatment a therapeutic amount of a compound of Formula I:

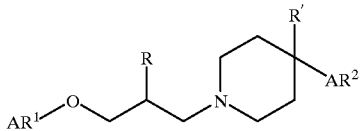

where:
- R and R' are independently hydrogen or hydroxy;
- AR$^1$ is phenyl, naphthyl, quinolinyl, isoquinolinyl, indanyl, 1,2,3,4-tetrahydronaphthyl, indolyl, N-(C$_1$–C$_4$ alkyl)indolyl, benzothiazolyl, benzothienyl, benzofuryl, 2,3-dihydrobenzothienyl, 2,3-dihydrobenzofuryl, julolidinyl, or dibenzofuryl, each optionally substituted with one or two substituents independently selected from the group consisting of C$_1$–C$_6$ alkyl, C$_1$–C$_6$ acyl, benzoyl, C$_1$–C$_6$ alkoxy, phenoxy, C$_1$–C$_6$ alkylthio, trifluoromethyl, trifluoromethoxy, or halo;
- AR$^2$ is pyridin-3-yl, quinolin-3-yl, isoquinolin-4-yl, or quinoxalin-2-yl; or pharmaceutically acceptable acid addition salts thereof.

10. A method of claim 9, where the mammal is a human.

11. A method for the treatment of anxiety disorders, comprising administering to a mammal in need of such treatment an effective dose of a compound of Formula I:

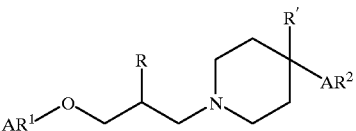

where:
- R and R' are independently hydrogen or hydroxy;
- AR$^1$ is phenyl, naphthyl, quinolinyl, isoquinolinyl, indanyl, 1,2,3,4-tetrahydronaphthyl, indolyl, N-(C$_1$–C$_4$ alkyl)indolyl, benzothiazolyl, benzothienyl, benzofuryl, 2,3-dihydrobenzothienyl, 2,3-dihydrobenzofuryl, julolidinyl, or dibenzofuryl, each optionally substituted with one or two substituents independently selected from the group consisting of C$_1$–C$_6$ alkyl, C$_1$–C$_6$ acyl, benzoyl, C$_1$–C$_6$ alkoxy, phenoxy, C$_1$–C$_6$ alkylthio, trifluoromethyl, trifluoromethoxy, or halo;
- AR$^2$ is pyridin-3-yl, quinolin-3-yl, isoquinolin-4-yl, or quinoxalin-2-yl; or pharmaceutically acceptable acid addition salts thereof.

12. A method of claim 11, where the mammal is a human.

13. A pharmaceutical formulation comprising an effective amount for deactivation of the 5-HT$_{1F}$ receptor of a compound of Formula I:

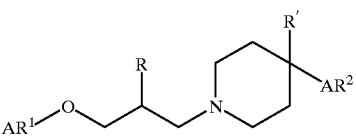

where:
- R and R' are independently hydrogen or hydroxy;
- AR$^1$ is phenyl, naphthyl, quinolinyl, isoquinolinyl, indanyl, 1,2,3,4-tetrahydronaphthyl, indolyl, N-(C$_1$–C$_4$ alkyl)indolyl, benzothiazolyl, benzothienyl, benzofuryl, 2,3-dihydrobenzothienyl, 2,3-dihydrobenzofuryl, julolidinyl, or dibenzofuryl, each optionally substituted with one or two substituents independently selected from the group consisting of C$_1$–C$_6$ alkyl, C$_1$–C$_6$ acyl, benzoyl, C$_1$–C$_6$ alkoxy, phenoxy, C$_1$–C$_6$ alkylthio, trifluoromethyl, trifluoromethoxy, or halo;
- AR$^2$ is pyridin-3-yl, quinolin-3-yl, isoquinolin-4-yl, or quinoxalin-2-yl; or pharmaceutically acceptable acid addition salts thereof, in combination with a suitable pharmaceutical carrier, diluent, or excipient.

* * * * *